(12) United States Patent
Van Duren et al.

(10) Patent No.: US 7,220,273 B2
(45) Date of Patent: May 22, 2007

(54) CONTROL OF AIRFLOW TO AN INFLATABLE THERMAL DEVICE

(75) Inventors: Albert Philip Van Duren, Chaska, MN (US); Allen Hamid Ziaimehr, Arden Hills, MN (US); John Paul Rock, Minneapolis, MN (US); Scott Douglas Augustine, Bloomington, MN (US); Gary Rabindranath Maharaj, Eden Prairie, MN (US)

(73) Assignee: Arizant Healthcare Inc., Eden Prairie, MN (US)

( * ) Notice: Subject to any disclaimer, the term of this patent is extended or adjusted under 35 U.S.C. 154(b) by 621 days.

(21) Appl. No.: 10/024,387

(22) Filed: Dec. 17, 2001

(65) Prior Publication Data

US 2002/0058974 A1    May 16, 2002

Related U.S. Application Data

(60) Division of application No. 09/546,078, filed on Apr. 10, 2000, now Pat. No. 6,447,538, which is a continuation-in-part of application No. 09/138,774, filed on Aug. 24, 1998, now Pat. No. 6,126,681.

(51) Int. Cl.
*A61F 7/00*    (2006.01)
(52) U.S. Cl. .................................................. 607/96
(58) Field of Classification Search ............ 607/96–98, 607/107, 27; 601/148, 16, 6; 606/27; 137/527.8; 251/65, 149.2
See application file for complete search history.

(56) References Cited

U.S. PATENT DOCUMENTS 2,882,923 A * 4/1959 Smolensky ............... 137/515.5
3,528,453 A * 9/1970 Dunkelis ................. 137/527.8
3,565,099 A * 2/1971 Huber ..................... 137/269.5

(Continued)

FOREIGN PATENT DOCUMENTS

JP          08322959          12/1996

(Continued)

OTHER PUBLICATIONS

EN-60601-2-35-1996 E: European Standard for medical electrical equipment, heating blankets, heating pads, heating mattresses, safety requirements, protection against electric shock, protection against mechanical hazard, radiation protection, fire protection, environmental conditions adopted by CENELEC, European Committee for Electrotechnical Standardization.

(Continued)

*Primary Examiner*—Roy D. Gibson
*Assistant Examiner*—Pete Vrettakos
(74) *Attorney, Agent, or Firm*—Terrance A. Meador

(57) ABSTRACT

Airflow provided through an air hose to the inlet port of an inflatable thermal device is controlled by a mechanical device disposed at an end of the air hose that is coupled to the inlet port. In response to coupling the end of the air hose to the inlet port, the mechanical device operates to open the end and permit air to flow through the air hose and the inlet port. In response to decoupling the end of the air hose from the inlet port, the mechanical device operates to block air from flowing through the end of the air hose.

6 Claims, 20 Drawing Sheets

U.S. PATENT DOCUMENTS

| | | | |
|---|---|---|---|
| 4,063,570 A * | 12/1977 | Mitchell et al. | 137/454.2 |
| 4,302,640 A | 11/1981 | Vicenzi et al. | |
| 4,316,182 A | 2/1982 | Hodgson | |
| 5,057,822 A | 10/1991 | Hoffman | |
| 5,159,981 A * | 11/1992 | Le | 166/325 |
| 5,230,611 A * | 7/1993 | Shelton | 417/437 |
| 5,300,098 A | 4/1994 | Phlipot | |
| 5,300,101 A | 4/1994 | Augustine et al. | |
| 5,300,102 A | 4/1994 | Augustine et al. | |
| 5,318,568 A * | 6/1994 | Kaufmann et al. | 607/107 |
| 5,320,092 A | 6/1994 | Ryder | |
| 5,324,320 A | 6/1994 | Augustine et al. | |
| 5,405,371 A | 4/1995 | Augustine et al. | |
| 5,522,543 A * | 6/1996 | Herzog | 239/1 |
| 5,626,129 A | 5/1997 | Klimm et al. | |
| 5,693,079 A * | 12/1997 | Van Duren | 607/104 |
| 5,706,801 A | 1/1998 | Remes et al. | |
| 5,716,721 A * | 2/1998 | Moysan et al. | 428/627 |
| 5,724,993 A * | 3/1998 | Dunfee | 128/874 |
| 5,785,723 A | 7/1998 | Beran et al. | |
| 5,819,857 A * | 10/1998 | Rohrer | 173/90 |
| 5,862,843 A * | 1/1999 | Corbitt, III | 141/350 |
| 5,865,171 A | 2/1999 | Cinquin | |
| 5,881,717 A | 3/1999 | Isaza | |
| 5,950,621 A | 9/1999 | Klockseth et al. | |
| 6,126,681 A * | 10/2000 | Van Duren et al. | 607/96 |
| 6,143,020 A * | 11/2000 | Shigezawa et al. | 607/96 |
| 6,220,282 B1 * | 4/2001 | Powell | 137/512 |
| 6,357,491 B1 | 3/2002 | Buchanan et al. | |
| 6,447,538 B1 * | 9/2002 | Van Duren et al. | 607/96 |
| 6,493,889 B2 * | 12/2002 | Kocurek | 607/104 |

FOREIGN PATENT DOCUMENTS

| | | |
|---|---|---|
| WO | 00/06904 | 10/2000 |

OTHER PUBLICATIONS

PCT Search Report for PCT/US99/07567.

* cited by examiner

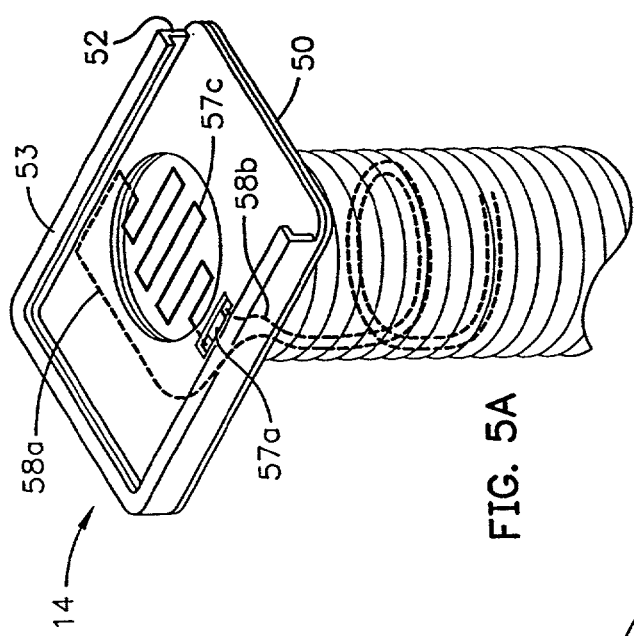
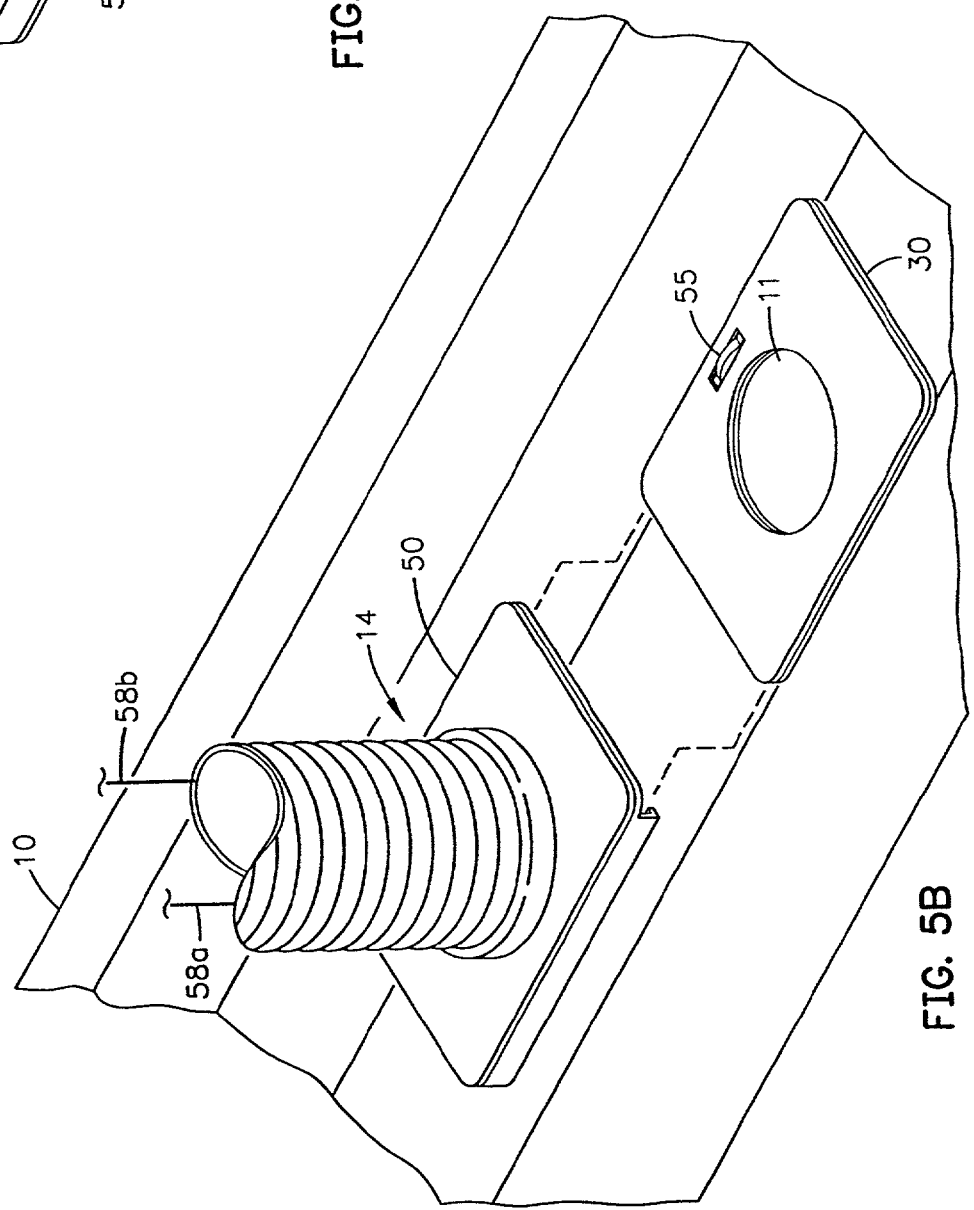
FIG. 5A
FIG. 5B

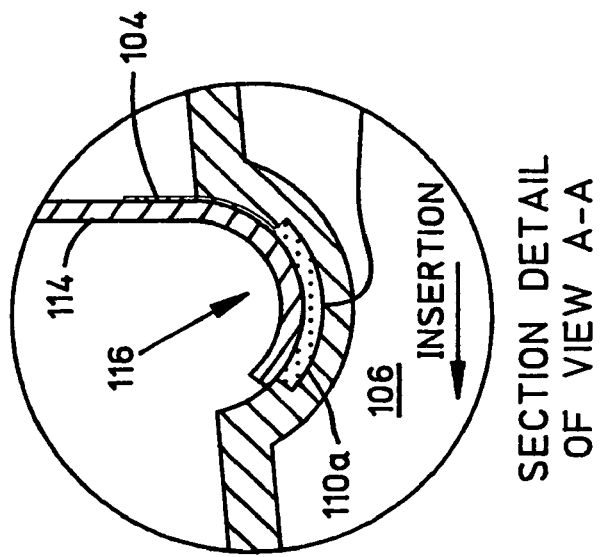
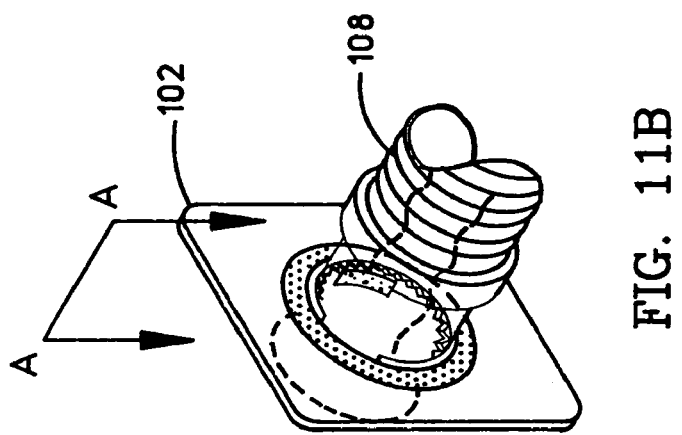
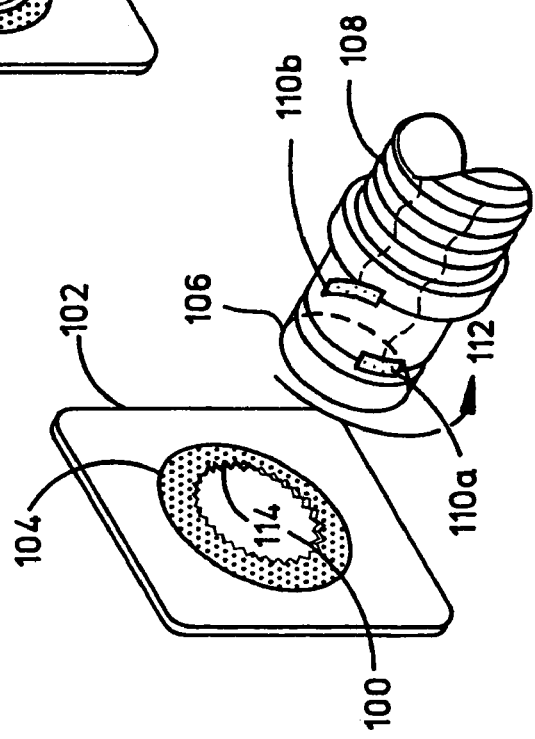
FIG. 11C
FIG. 11B
FIG. 11A

CONTROL OF AIRFLOW TO AN INFLATABLE THERMAL DEVICE

This is a divisional of application Ser. No. 09/546,078, entitled CONTROL AND DETECTION OF A CONDITION BETWEEN AN INFLATABLE THERMAL DEVICE AND AN AIR HOSE IN A CONVECTIVE WARMING SYSTEM, invented by Van Duren et al., and filed on April 10, 2000, now U.S. Pat. No. 6,447,538 which is a continuation in part of prior application Ser. No. 09/138,774, entitled DETECTION OF A CONDITION BETWEEN AN INFLATABLE THERMAL DEVICE AND AN AIR HOSE IN A CONVECTIVE WARMING SYSTEM, invented by Van Duren et al., and filed on Aug. 24, 1998 now U.S. Pat. No. 6,126,681.

BACKGROUND OF THE INVENTION

This invention relates to pressurized thermal systems that regulate human core temperature by convecting pressurized, thermally regulated air. More particularly, the invention relates to inflatable thermal blankets and the like that are used, for example, in a medical setting to deliver a bath of pressurized air which is heated, cooled, or ambient temperature, for the treatment of hypothermia or hypothermia. In particular, pressurized, thermally regulated air is used to inflate such a device and is expelled therefrom onto a person or animal. Still more particularly, the invention relates to controlling the flow of pressurized air through the end of an air hose in response to coupling and decoupling the end to the inlet port of an inflatable thermal device.

The International Electrotechnical Commission has promulgated a new standard (IEC 601-2-35) entitled Particular requirements for safety of blankets, pads and mattresses, intended for heating in medical use. This standard imposes requirements on the design and operation of convective warming systems. In particular, clause 46.101 states: "If omission of a part, or the interchange of parts of a multi-part heating device, will cause a safety hazard, the heating device shall be designed such that heat will be supplied only if all parts of the heating device are correctly positioned." This requirement is intended to prevent human or equipment error leading to patient injury.

In convective warming systems, a pressurized thermal device is used to deliver a bath of pressurized, thermally-regulated air to a person, animal, or thing. The device is inflated with the pressurized, thermally-regulated air and has one or more surfaces adapted for expelling the air onto a person. Such devices may lie on a person, around a person, or under a person. U.S. Pat. Nos. 5,324,320 and 5,405,371, for example, describe inflatable thermal blankets that lie on a person, expelling pressurized, warmed air through a lower surface that faces the person. U.S. Pat. No. 5,300,101 describes another inflatable thermal device that lies around the sides and at least one end of a person. Other kinds of inflatable thermal devices are contemplated, including those lying under a person. Therefore, when used, the term "inflatable thermal device" is intended to invoke any and all blankets, pads, mattresses, covers, and equivalent structures that operate as just described.

Typically, the inflatable thermal devices of interest convect pressurized air in response to a pressurized flow of warmed, cooled, or ambient temperature air that is provided, for example, from a heater/blower unit through an air hose. Typically the inflatable device includes one or more inlet ports that receive one end of the air hose. The other end of the air hose is received in the heater/blower unit. When the heater/blower unit is turned on, air is warmed in the unit and pumped from the unit through the air hose to inflate the inflatable thermal device, whence the air is exhausted to warm or cool a person. Such devices may exhaust the air through a plurality of punched holes, through porous material, or through air permeable material.

One hazard in convective warming systems that use inflatable devices is the risk of overheating or burning a person. In the first instance, the air temperature may exceed a level necessary for proper treatment. In the second instance, the end of the air hose that is received in an inlet port may become dislodged and repositioned in such a way as to direct the pressurized, heated air flow directly onto a person. It is these hazards that are contemplated by the IEC standard. To date, means for detecting and mitigating these hazards have not been incorporated into the convective warming systems described above. Furthermore, in addition to the hazards contemplated by the new IEC standard, there is an operating deficiency common to many commercially available convective warming systems. This deficiency lies in the dependence of the air flow temperature at the distal end of an air hose on several environmental and design conditions which prevent accurate estimation of air hose outlet temperature.

The commercially available heater/blower units for convective warming systems include a heater and a blower which operate to provide a steady stream of temperature-conditioned air at a given mass flow. The temperature of the heated air ducted from the heater/blower unit through an air hose is tightly controlled at the heater/blower unit end of the air hose; however, the temperature of air flow introduced into the inflatable thermal device is a function of several factors, including, but not limited to: 1.) the thermal capacity of the unit; 2.) the blower capacity; 3.) the length, thermal conductivity, and thermal emissivity of the air hose between the unit and the device; 4.) the fluid flow resistance of the device; and, 5.) the ambient conditions, of which temperature and external air velocity are the most important.

The exhaust (output) temperature of the flow of air leaving a heater/blower unit is generally tightly controlled by a unit temperature controller. The temperature controller continually senses the output temperature at a port in the unit where the proximal (near) end of the air hose is received and adjusts the heater unit power to maintain the output temperature at constant setting. The temperature of the air flow at the distal (far) end of the air hose (that is, the inlet temperature to the inflatable thermal device), however, depends greatly on the conditions listed above.

With most of the presently available heater/blower systems, it is also possible to interconnect the blower units, hoses, and thermal blankets of different manufacturers. Because these components may not have been designed to work together, and because there are not always common standards, the patient can be inadvertently supplied with air at inappropriate flow rates and temperatures. Not only can the patient be harmed, it is also possible to damage the equipment. Further, some users may knowingly use equipment that is not designed to work together out of convenience. Clearly visible electrical contact points permit operators to bypass interlock safeguards. The concern for the improper use of equipment must be tempered with the ability to warm patients in emergency situations.

Accordingly there is a need to: 1.) prevent heater/blower unit misuse when the inflatable thermal device has been disconnected from the air hose; 2.) provide better control of air flow temperature at the distal end of the air hose irrespective of ambient conditions, resistive load of the inflatable thermal device, or heater/blower unit capability; and 3.) meet the requirements of the IEC standard.

SUMMARY OF THE INVENTION

The invention is based on the critical realization that the junction between the distal (far) end of an air hose and an inlet port of an inflatable thermal device provides a location where the continuity of the air flow path can be regulated.

In this regard, flow of air to the inflatable thermal device is controlled mechanically, with the insertion of the distal end of the air hose into the inflatable thermal device. Several valve mechanisms can be used to block air flow from the air hose when the hose is not properly seated in the inlet port. When inserted, the valves are forced open to provide air to the inflatable thermal device.

Accordingly, it is an object to invent a convective warming system that includes a pressurized thermal device with the ability to react to air flow conditions at a point where an air flow is provided through an inlet port of the device.

Another object is to disable, prevent, or attenuate the operation of a convective warming system when the inflatable thermal device becomes detached from a heater/blower unit.

These and other objects and advantages of this invention will become evident when the following detailed description is read in conjunction with the below-described drawings.

BRIEF DESCRIPTION OF THE DRAWINGS

FIGS. 5A–5D, illustrate the elements of FIGS. 3A and 3B with the addition of an airflow sensor located in the distal end;

FIGS. 11A through 11C illustrate the inflatable thermal device where the inlet port includes a hose card.

DETAILED DESCRIPTION OF THE PREFERRED EMBODIMENTS

Figure 1:
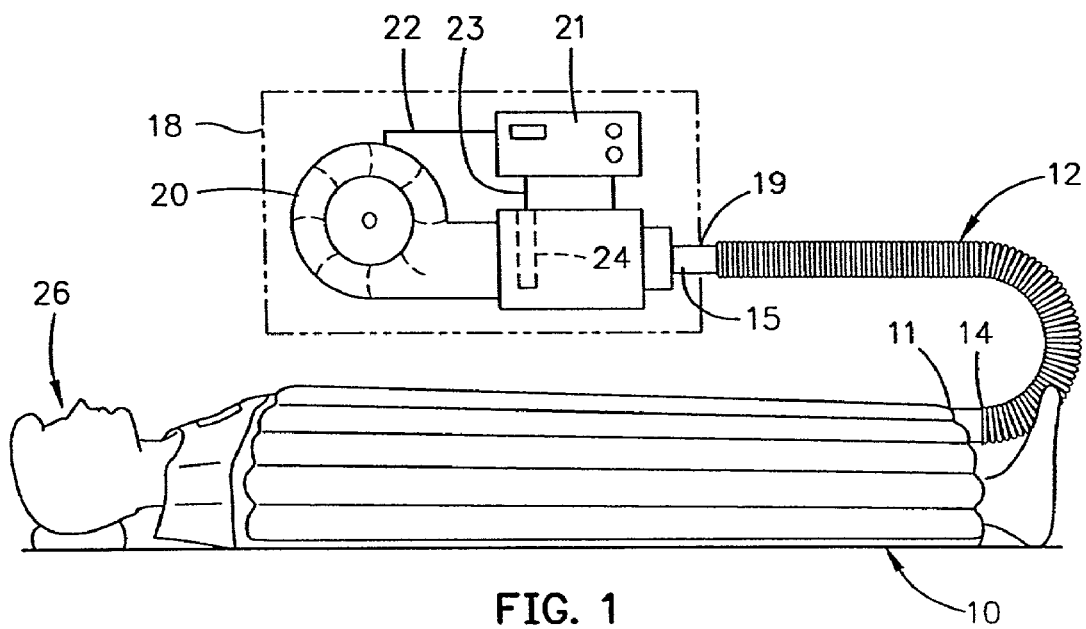
FIG. 1. Is an illustration of a convective warming system in which the invention may be embodied.

FIG. 1 illustrates a convective warming system that is operated to control the body temperature of a person by convecting thermally-regulated air from an inflatable thermal device in the direction of the person's skin. The convective warming system of FIG. 1 provides a stream of pressurized, thermally-regulated air to an inflatable thermal device through an inlet port of the device. In FIG. 1, the inflatable thermal device is an inflatable thermal blanket, of the type sold by Augustine Medical, Inc. under the BAIR HUGGER® trademark. This, however, is for purposes of illustration only. In fact, any and all equivalent inflatable thermal devices including blankets, pads, mattresses, covers, and equivalent structures are intended to enjoy the benefits of this invention.

With greater specificity, the convective warming system of FIG. 1 includes an inflatable thermal device 10 having one or more inlet ports through which a flow of pressurized, thermally-regulated air is admitted to inflate the inflatable thermal device 10. One such inlet port is indicated by reference numeral 11. In the BAIR HUGGER® family of inflatable thermal blankets, inlet ports typically comprise an opening into an inflatable structure and a stiff planar member of cardboard having an aperture. The planar member of cardboard is mounted to the inflatable structure such that the aperture in the member is aligned with the opening in the inflatable structure. The planar member is commonly referred to as a "hose card" because it provides a flat, card-like structural element that receives and supports the distal end of an air hose when the distal end is joined, mated, coupled or received in the inlet port. However, this invention is not intended to be limited to an inflatable thermal device with such inlet ports. Furthermore, an inflatable thermal device may include more than one inlet port. In this regard, many models of inflatable thermal devices have two—and sometimes more—inlet ports located at various positions in order to provide flexibility in arranging the elements of a convective warming system.

In the convective warming system of FIG. 1, the inflatable thermal device 10 is inflated by a stream of pressurized, thermally-regulated (warmed or cooled) air provided through an air hose 12 having a distal (far) end 14 and proximal (near) end 15. The distal end 14 is joined, mated, coupled, or received in one of the inlet ports of the inflatable thermal device 10. In FIG. 1, the distal end 14 is received in the inlet port 11. In other words, the inlet port 11 and the distal end 14 form a junction through which an air flow is provided to inflate the inflatable thermal device 10. A heater/blower unit 18 generates and provides a flow of pressurized, thermally-regulated air (hereinafter referred to as "an airflow"). In this regard, the unit 18 includes a port 19 in which the proximal end 15 of the air hose 12 is received. Through the port 19, the proximal end 15 is coupled, mated, received in, or otherwise joined to an outlet of a blower 20. The unit 18 includes a control unit 21 with user-accessible controls that may be used to set levels or magnitudes of air flow heat and air flow velocity. A signal for air flow velocity is provided by the control unit 21 on signal path 22 where it is coupled to the blower 20 to control the speed of a blower motor (not shown) that propels air through the blower 20. The control unit 21 further generates a signal on signal path 23 that controls the operation of a heater 24 disposed near the outlet of the blower 20 for heating the air flow. Heater/blower units with user-accessible controls as just described are commercially available. Examples are the 200, 500, and 700 series warming units available from Augustine Medical, Inc.

In the example selected for illustration of the convective warming system of FIG. 1, the inflatable thermal device 10 is placed on a person 26. This is not intended to limit the application of this invention to warming only or to use with humans. Indeed, it may be used in any system that thermally regulates persons, animals, or things using an inflatable thermal device.

Figure 2:
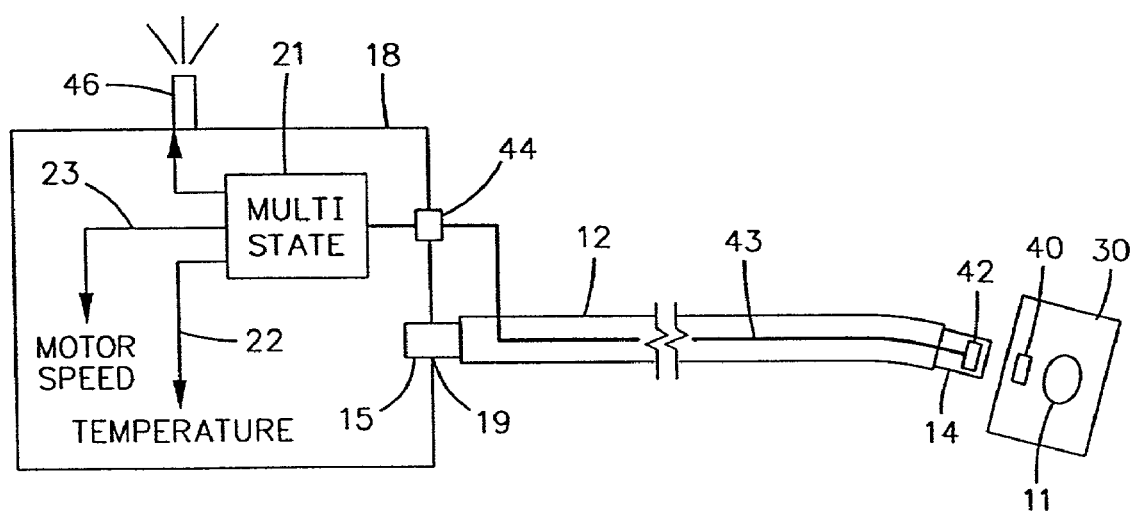
FIG. 2 is a block diagram showing the elements of a convective warming system.

Refer now to FIG. 2. In FIG. 2, a convective warming system includes an inflatable thermal device (not shown) having one or more inlet ports, one of which is indicated by reference numeral 11. The distal end 14 of the air hose 12 is intended to be coupled to or received in the inlet port 11; however, these elements are shown separated in FIG. 2. The proximal end 15 of the air hose 12 is received in the port 19 of the heater/blower unit 18. The just-described elements may be combined with a combination of elements that operate cooperatively to detect a condition between the distal end 14 of the air hose 12 and the inlet port 11 of the inflatable thermal device. These elements include a first circuit element 40 that is disposed in, on, at or near the inlet port 11. For example, the first circuit element 40 may be formed an as integral part of a hose card 30. A second circuit element 42 is located in, on, at, or near the distal end 14 of the air hose 12, and a signal path including one or more signal conductors 43 extends in or along the air hose 12 to the proximal end 15. At or near the proximal end 15 of the air hose 12, the signal path 43 is connected at connector 44 to the control unit 21 of the heater/blower unit 18. The combination of elements 40, 42 and 43 provides a circuit for detecting a condition that may develop or exist between the distal end 14 of the air hose 12 and the inlet port 11. In other words, these elements enable the generation, conduction, or detection of a signal that represents the condition. Such a condition may be embodied, for example, in the disengagement of the distal end 14 from the inlet port 11 while the heater/blower unit 18 is operating. Another condition, for example, could include a change in the temperature of the air flow through the distal end 14 or the inlet port 11, or through the junction formed between the distal end 14 and the inlet port 11 while the heater/blower unit 18 is operating. Yet another condition may be a change in the air flow velocity through the distal end 14 or the inlet port, or through the junction formed between the distal end 14 and the inlet port 11 while the unit 18 is operating. In this latter regard, the inverse of the condition would correspond to a decrease in the air flow resistance or a decrease in the air pressure at the distal end 14 of the air hose 12 or the inlet port 11, or in the junction between the distal end 14 and the inlet port 11 while the unit 18 is operating. Whatever the condition or conditions that these elements are deployed to detect, sensing is provided by cooperative operation between the first circuit element 40 and the second circuit element 42 when the distal end 14 is joined, mated, coupled or received in the inlet port 11. In this regard, the junction formed between the distal end 14 and the inlet port 11 brings the first and second circuit elements 40 and 42 into close proximity and/or alignment. For so long as the proximity and/or alignment is maintained while the heater/blower unit 18 is operating, a first indication or signal may be generated and conducted on the signal path 43 to the control unit 21. A change in the condition is sensed by the cooperative operation of the first and second circuit elements 40 and 42, with the change in condition causing a change in the signal conducted on 43. A change in the signal conducted on 43 that is observed by the control unit 21 while the heater/blower unit 18 is operating causes the control unit 21 to take any one or more of a number of actions. First, the control unit 21 may simply cause the generation of a perceptible indication. In this regard, an indicator 46 may provide a visual and/or audible indication of a changed condition. In addition, or alternatively, the control unit 21 may respond to a change in condition by changing the motor speed of the blower 20 and/or the temperature of the warming element 24. Further, the control unit 21 may be designed or adapted to shut down or stop the operation of the heater/blower unit 18 altogether, or to place it in a standby state during which the temperature and/or velocity of the flow of air may be reduced.

The cooperative operation of the first and second circuit elements can also provide a "first necessary condition" for starting the heater/blower unit 18, preventing it from being turned on, or becoming fully operational after being turned on, in response to disconnection or non-connection of the distal end 14 and the inlet port 111 prior to operation of the heater/blower unit 18. Stated another way, the heater/blower unit 18 may be turned on, or be fully operational only upon detection of joinder, coupling, or mating of the distal end 14 with the inlet port 11.

Figure 3A:
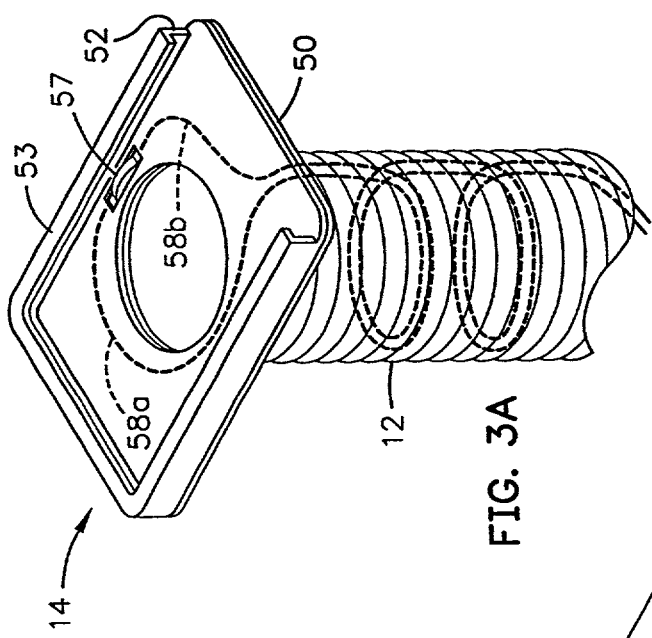
FIGS. 3A and 3B illustrate an air hose, an inflatable thermal device and elements of a presence sensor that monitors continuity of the connection between the distal end of the air hose and an inlet port of the device.
Figure 3B:
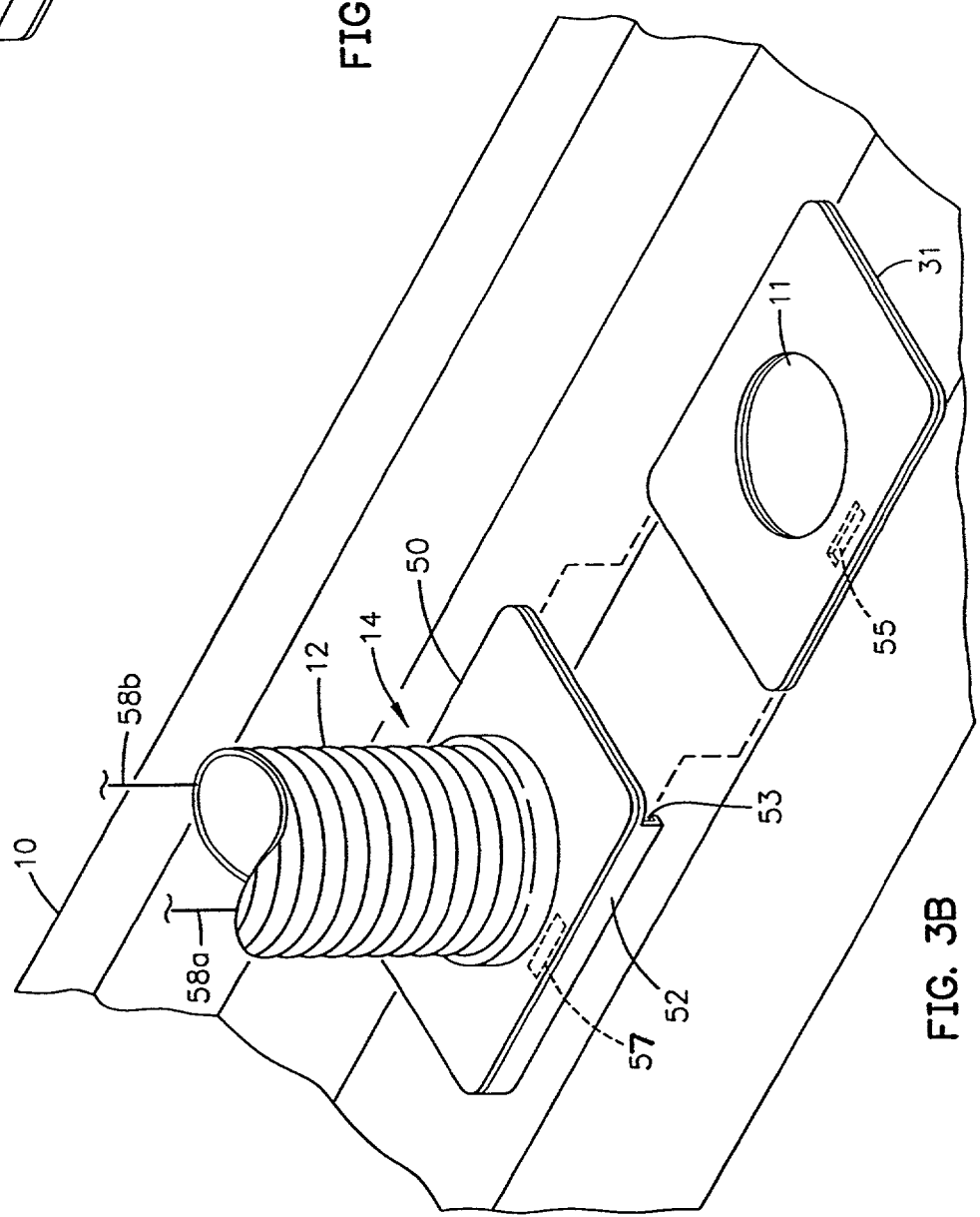

FIGS. 3A and 3B illustrate how mating of the air hose distal end with the inlet port is detected and indicated. Although these figures illustrate an inlet port of a certain construction, those skilled in the art will realize that the principles represented in these figures can be applied to other air hose/inlet port configurations. In FIGS. 3A and 3B, the hose card 30 is shown mounted on the inflatable thermal device 10 at the inlet port 11. The distal end 14 of the air hose has mounted to it a mechanism that aligns the distal end 14 with the inlet port 11 thereby to join, couple, or mate these elements, or otherwise form a junction between them. The mechanism includes a planar member 50 having generally the same shape and construction as the hose card 30 with the addition of an extending edge 52 that transitions into a lip 53. The extending edge 52 extends substantially along three sides of the periphery of the planar member 50 so that the distal end 14 can be joined, mated, coupled or received in the inlet port 11 by engaging the edges 31 of the hose card 30 between the lip 53 and a surface of the planar member 50. In FIGS. 3A and 3B, a first circuit element 55 is incorporated into the structure of the hose card 30 laterally of the opening in the hose card 30 that communicates with the inlet port 11. A second circuit element 57 is disposed in the planar member 50 laterally of the opening in the distal end 14 of the air hose 12. One or more signal conductors 58 are disposed in (or on) the air hose 12, extending from the distal end 14, along the air hose 12 toward its proximal end (not shown in these figures). Integration of signal wires into an air hose is within the ambit of modern manufacturing technology. Reference is given, for example, to vacuum cleaner hoses with embedded power conductors. In the figures, two electrical wires 58a and 58b are shown: their purpose is to conduct signals to the control unit 21. When the hose card 30 is received between the lip 53 and the planar member 50 so that the opening in the distal end 14 is aligned with the inlet port 11, the first circuit element 55 and the second circuit element 57 cooperate to complete or close a circuit between the one or more conductors 58a and 58b that is connected to the control unit 21. Many possible configurations of this circuit are possible for implementing as much of the invention as is illustrated in FIGS. 3A and 3B. For example, the first circuit element 55 may comprise a magnetic member and the second circuit element 57 may comprise a reed switch or a Hall effect device. In this case, when the first and second circuit elements 55 and 57 are placed in close proximity by mating of the distal end 14 with the inlet port 11, the magnetic member 55 causes the reed switch to close, connecting the two electrical conductors 58*a* and 58*b*, thereby creating a signal pathway along which a signal may be conducted. Conversely, when the distal end 14 is disengaged from the inlet port 11, the first and second circuit members 55 and 57 will be moved apart, causing the reed switch to open, which will disable, interrupt or open the signal path just described. This of course will prevent the conduction of a signal. Other mechanisms may be used for the first and second circuit elements 55 and 57 and for the one or more conductors 58*a* and 58*b*. For example, the first circuit element 55 may comprise a spring-loaded bar of conductive material, while the second circuit element 57 may comprise two spaced-apart terminals or posts to which the electrical conductors 58*a* and 58*b* are respectively connected. When the first and second circuit elements 55 and 57 are in close proximity, it is contemplated that the conductive bar in the hose card 30 would span and contact the posts, providing a conductive path therebetween. In yet another alternate implementation, the first circuit element 55 may comprise a spring-loaded, protruding member and the second circuit element 57 could comprise a mechanical switch that is operated by the protruding member when the distal end 14 is joined to the inlet port 11. In yet another implementation, the circuit could be an optical one in which the conductors 58*a* and 58*b* are optical fibers that terminate in optical connectors in the second circuit element 57. In this case, the first circuit element 55 could include an optical coupler that would complete an optical signal path between the ends of the two optical conductors. Alternatively, means exist for implementing an optical circuit using a single optical fiber terminated at the second circuit element 57 and a mirror incorporated in the first circuit element 55.

The first and second circuit elements 55 and 57 in FIGS. 3A and 3B operate cooperatively to provide a sensor-like function. In this regard, the sensor could be termed a "presence" sensor in that it senses the presence of the inlet port 11 from the standpoint of the distal end 14, or, conversely, it senses the presence of the distal end 14 with respect to the inlet port 11. From another point of view, the first and second circuit elements operate cooperatively as a switch with OPEN and CLOSED positions. The OPEN position would indicate separation or disconnection between the distal end 14 and the inlet port 11 or discontinuity of the junction formed between the distal end 14 and the inlet port 11. The CLOSED position, on the other hand, would indicate joining or connection of the distal end 14 with the inlet port 11, or continuity of the junction formed therebetween.

Figure 4A:
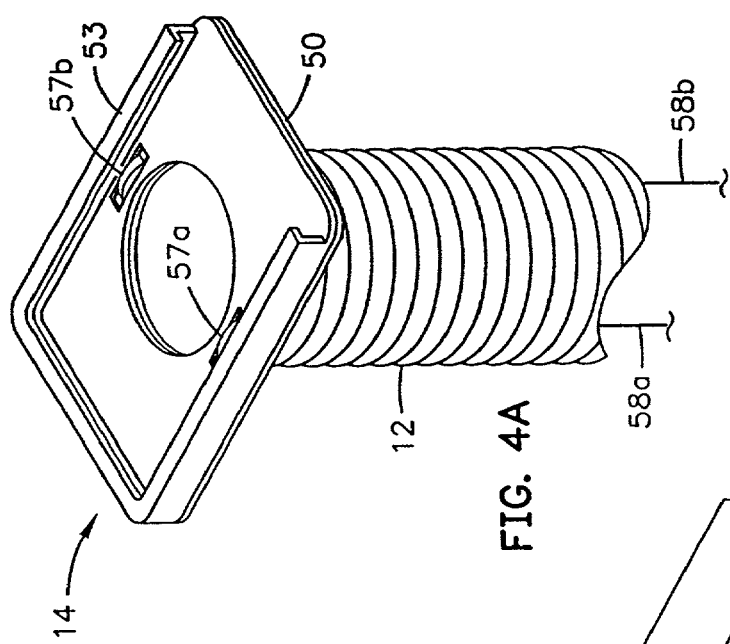
FIGS. 4A and 4B illustrate the elements of FIGS. 3A and 3B, with the addition of an airflow sensor located at the inlet port.
Figure 4B:
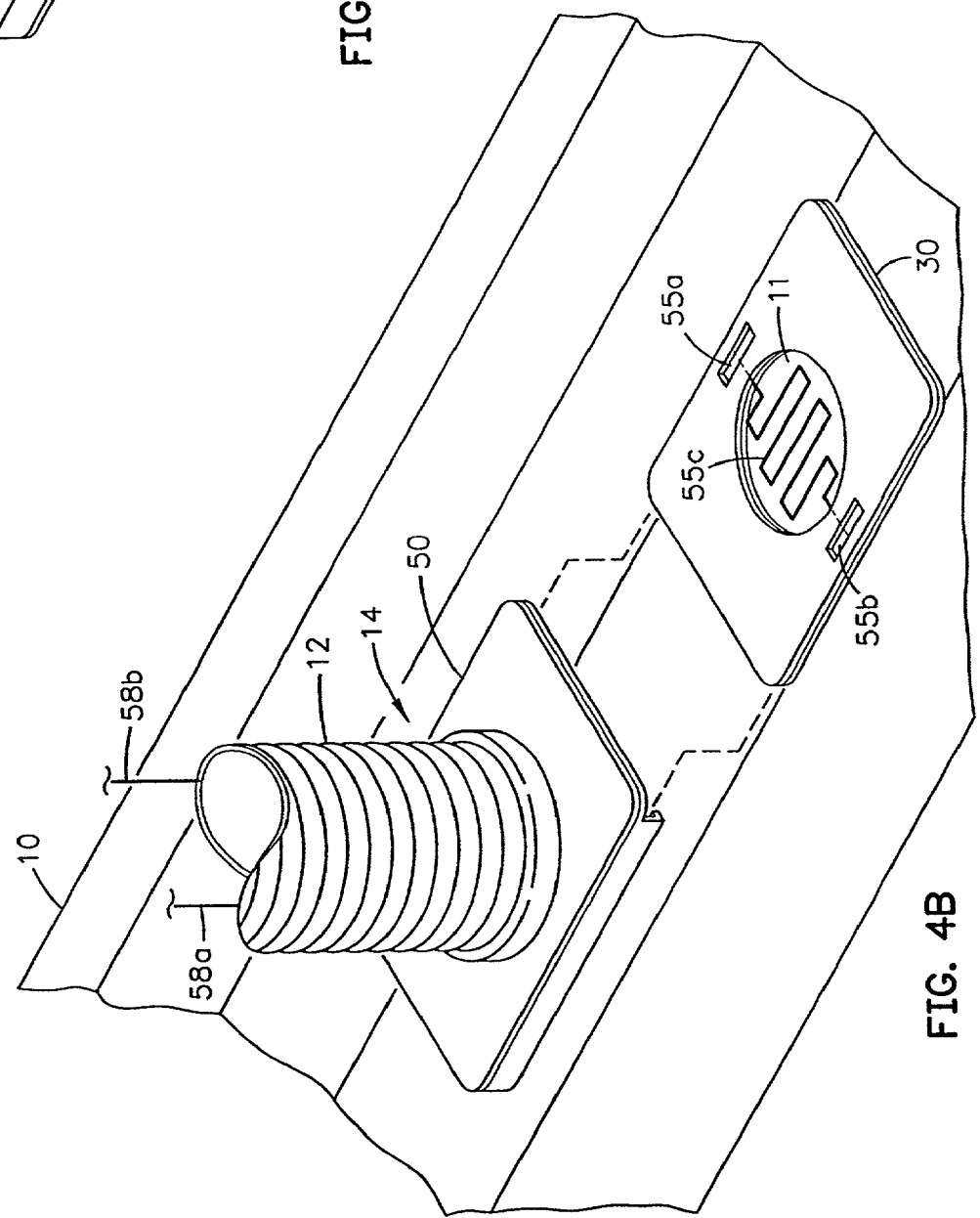

FIGS. 4A and 4B illustrate how the information provided by the simple two-state switch of FIGS. 3A and 3B can be enriched by provision of an air flow sensor at the junction formed between the distal end 14 and inlet port 11. In the description an Aair flow sensor≅ is a sensor that detects one or more air flow conditions and causes generation of a signal having a component that reports the magnitude of the sensed conditions(s). The air flow conditions may include, for example, temperature and velocity. In FIGS. 4A and 4B, the first circuit element comprehends a first conductive contact element 55*a*, a second conductive contact element 55*b* and a sensor 55*c*. The first and second elements 55*a* and 55*b* are physically and electrically connected to the sensor 55*c*, which is disposed in the opening of the hose card 30 in alignment with the inlet port 11. Again, the elements 55*a*, 55*b*, and 55*c* are integrated into the structure of the hose card 30, although this is not intended to limit the implementation of a sensor at the junction between the distal end 14 and the inlet port 11. The second circuit element includes first and second conductive contact elements 57*a* and 57*b* disposed in the planar member 50 laterally of the opening in the distal end 14. When the planar member 50 fully engages the hose card 30 to join the distal end 14 with the inlet port 11, the contact element 55*a* mechanically and electrically contacts the contact element 57*a*, while the contact element 55*b*, physically and electrically contacts the contact element 57*b*. The electrical conductors 58*a* and 58*b* are connected, respectively, to the second circuit element contact elements 57*a* and 57*b*. Now, when the hose card 30 is engaged by the planar member 50, the presence sensor function will be performed by completion of an electrical signal path comprising 58*a*, 57*a*, 55*a*, 55*c*, 55*b*, 57*b*, and 58*b*. In addition, the sensor 55*c*, being disposed in the junction formed between the distal end 14 and the inlet port 11 provides the ability to sense and indicate characteristics of the air flow in the junction. In this regard, assuming that the sensor 55*c* comprises a thermocouple, the temperature of the air flow could be measured and reported in the form of a signal. The sensor 55*c* could also be configured to sense the velocity of the air flow at the same point using a hot-wire anemometer, for example. Moreover, two sensors and two circuits could be incorporated in the manner illustrated in FIGS. 4A and 4B to indicate presence, air flow temperature, and air flow velocity, or any combination thereof. Manifestly, optical elements exist which may be assembled using FIGS. 4A and 4B and the description just given to implement presence, temperature, and/or pressure sensing at the junction between the distal end 14 and inlet port 11.

FIGS. 5A and 5B illustrate disposition of a sensor in, at, on, or near the distal end 14. In this case, the first circuit element 55 may comprise a magnetic piece, a spring-loaded activator for a mechanical switch, or spring-loaded conductive strip. At the distal end 14, the second circuit element includes a terminal element 57*a* and a sensor element 57*c*. The terminal element 57*a* operates cooperatively with the first circuit element 55 to complete an electrical circuit allowing the sensor 57*c* to operate in the junction between the distal end 14 and inlet port 11. In this case, the contact element 57*a* may comprise a reed switch, a Hall effect device, a mechanical switch, or two conductive posts, while the sensor element 57*c* may comprise a thermocouple or an air velocity sensor. As with the example illustrated in FIGS. 4A and 4B, the examples of FIGS. 5A and 5B may incorporate more than one sensor at or near the distal end 14 and may sense presence, temperature and/or velocity. Furthermore, optical elements exist that could be incorporated to provide an analog of the electrical circuit shown in FIGS. 5A and 5B.

Figure 5C:
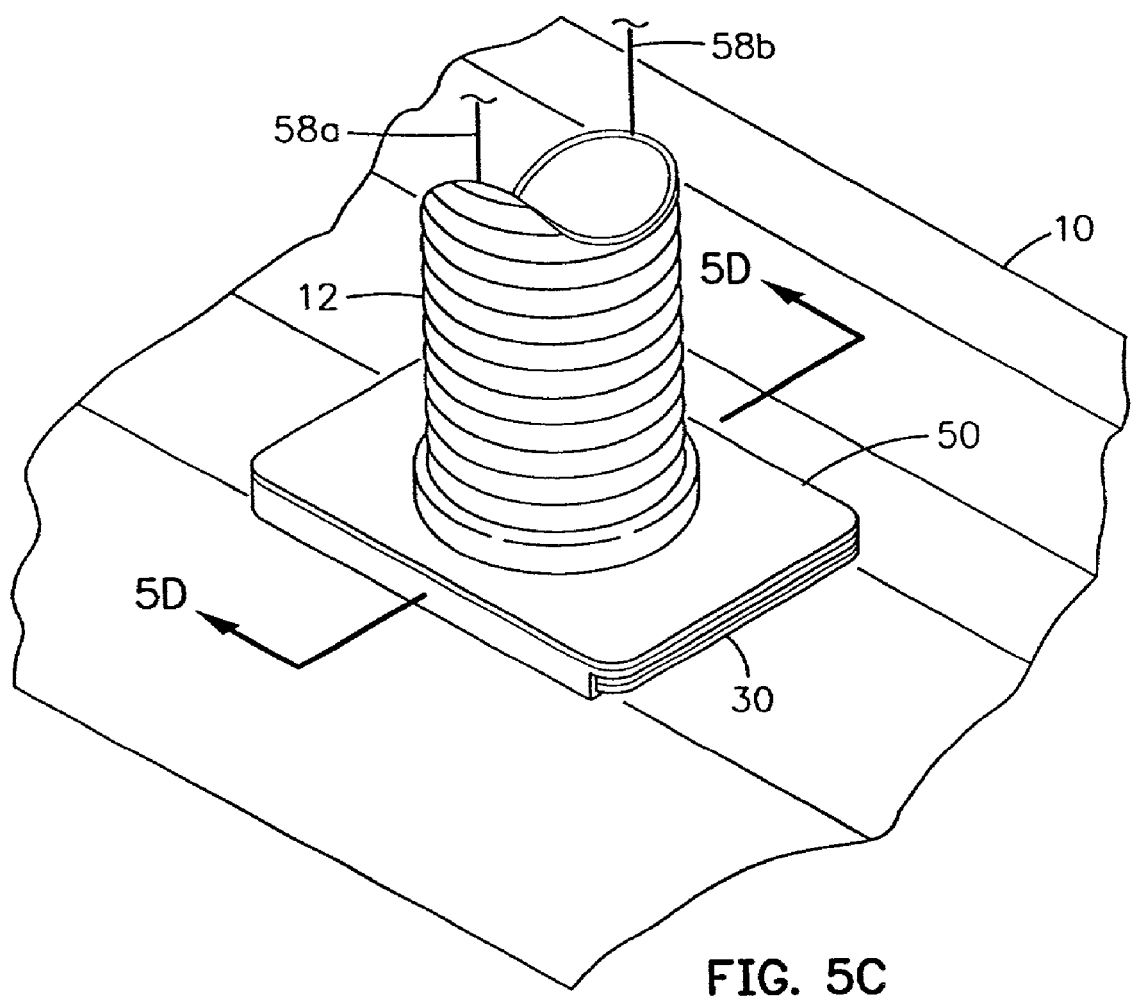
Figure 5D:
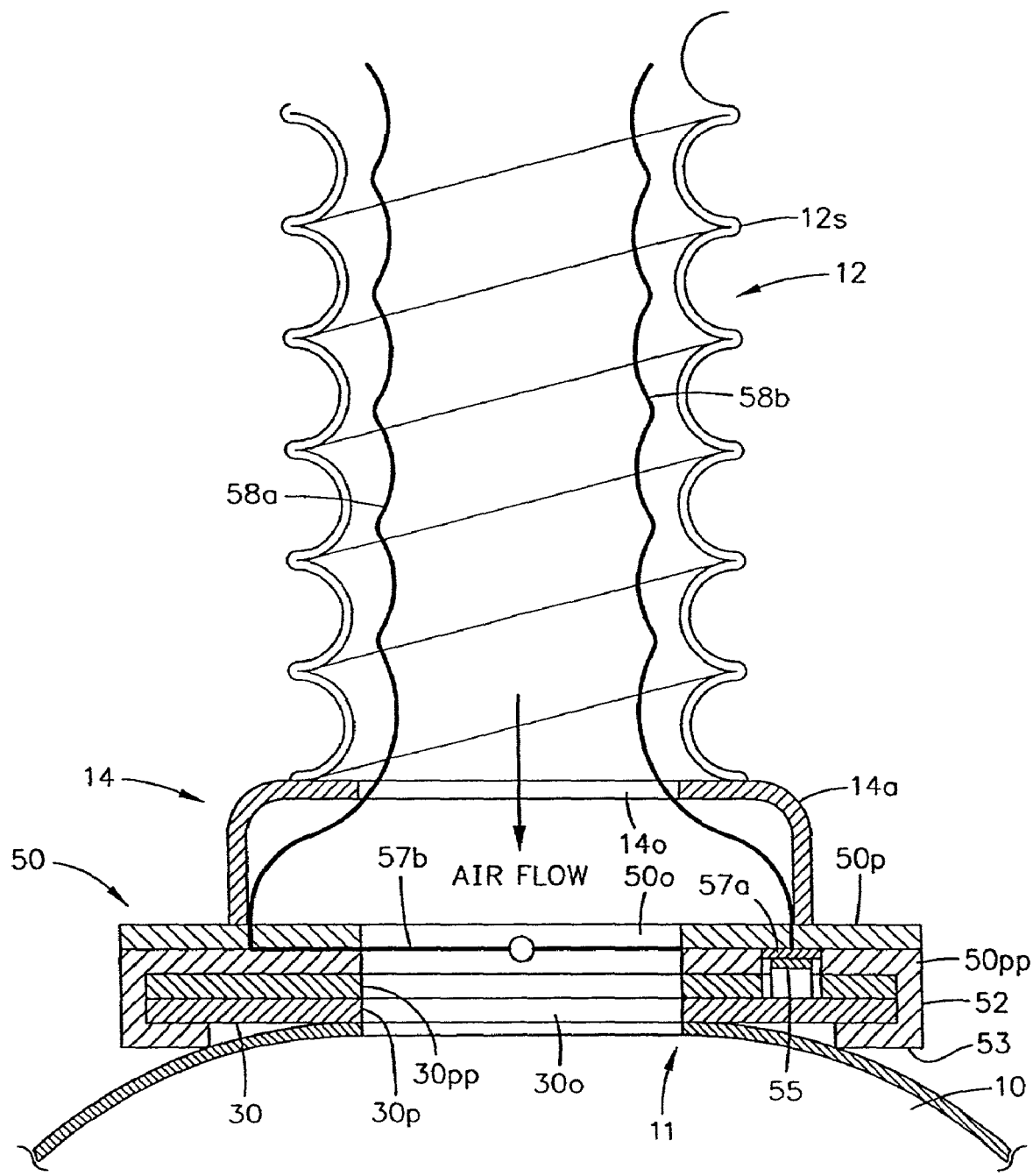

FIGS. 5C and 5D continue the illustration presented in FIGS. 5A and 5B. FIG. 5C shows the planar member 50 engaged with the hose cord 30 thereby to join, couple, or mate the distal end 14 with the inlet port 11. FIG. 5D is a side sectional elevation view taken along lines D—D in FIG. 5C. In FIG. 5D, the air hose 12, has a conventional construction that includes a flexible side wall 12*s*. In addition, the conductors 58*a* and 58*b* are embedded in, formed in, or attached to the side wall 12*s*. The air hose 12 terminates at the distal end 14 in a cup-shaped plastic member 14*a* having a disk-shaped opening 14*o*. The rim of the plastic member 14*a* is attached to the planar member 50. The planar member 50 includes a first plate 50*p*, preferably a plastic piece to which the rim of the plastic member 14a is bonded or joined. Another plastic piece 50pp is attached to the plastic piece 50p; this piece 50pp includes the extending side wall 52 and the lip 53. The pieces 50p and 50pp are joined or otherwise bonded together to form the planar member 50 as a single, unitary piece. The thermocouple 57c is held between the two pieces 50p and 50pp and includes a portion that extends across an opening 50o provided through the planar member 50. The hose card 30 includes two planar pieces 30p and 30pp that are glued or bonded together. An opening 30o in communication with the inlet port 11 aligns with the openings 50o and 14o so that an air flow path extends through the air hose 12 and the openings 14o, 50o and 30o. One contact 57a is fixed in the planar member 50 at a location where it is contacted by the shorting bar 55 when the planar member 50 is seated on the hose card 30 as shown in FIGS. 5C and 5D.

Figure 6A:
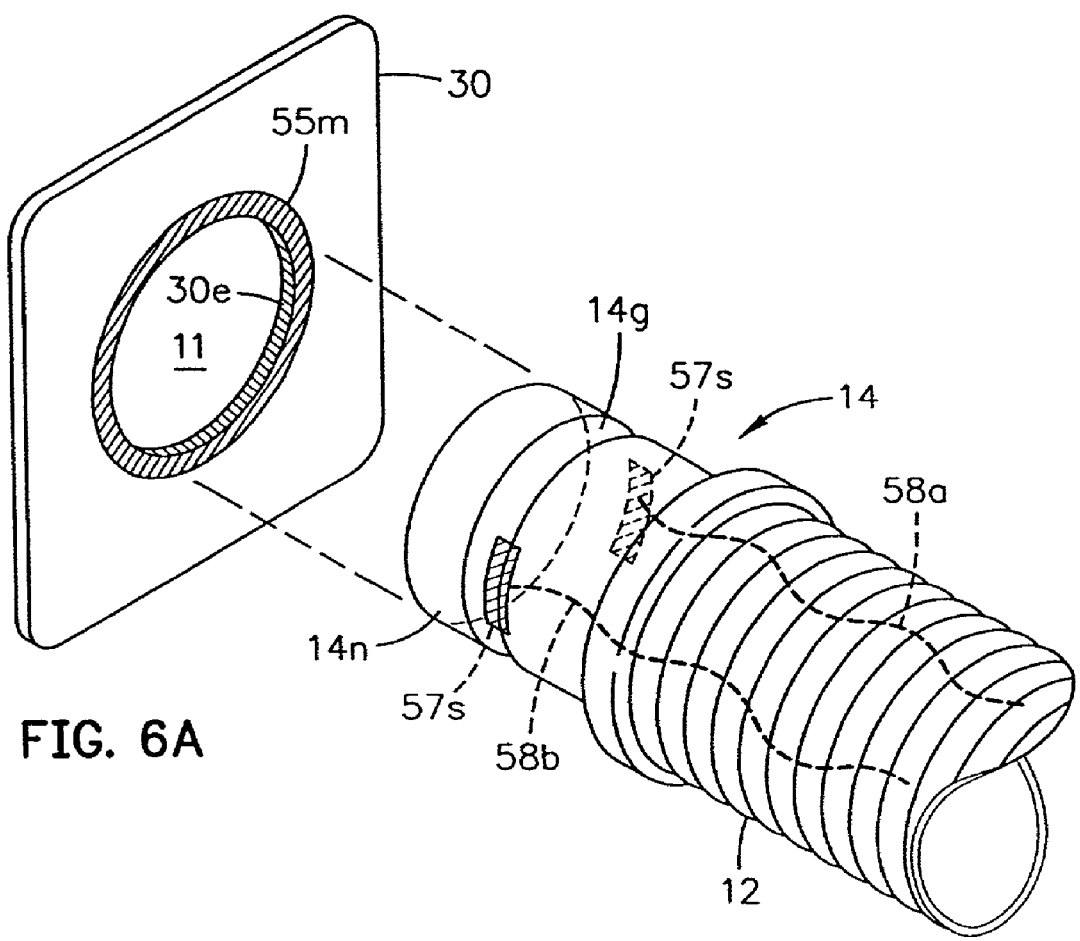
FIGS. 6A and 6B illustrate an alternate embodiment of the presence sensor of FIGS. 3A and 3B.
Figure 6B:
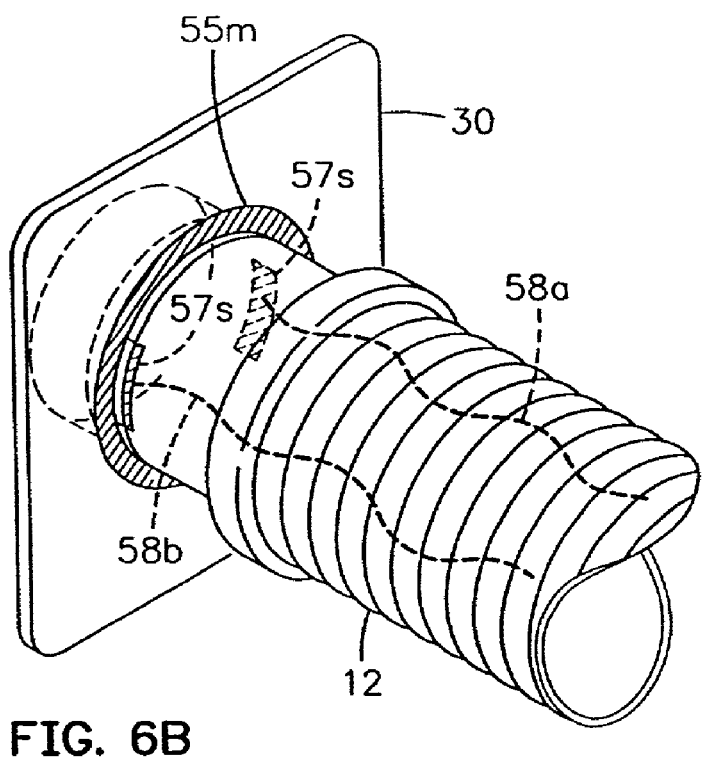

FIGS. 6A and 6B illustrate an alternative embodiment of a presence sensor in which the opening in the center of the hose card 30 includes an edge 30e on and adjacent to which a conductive material 55m is disposed. The distal end 14 of the air hose 12 is configured as a nozzle 14n having a circumferential groove 14g in which two strips of conductive material 57s are disposed. Each of the strips 57s is connected to a respective one of the conductors 58a and 58b so that when the nozzle 14n is inserted into the hole in the hose card 30, the groove 14g seats on the edge 30e and the material 55m completes or closes an electrically conductive pathway between the strips 57s.

Figure 7:
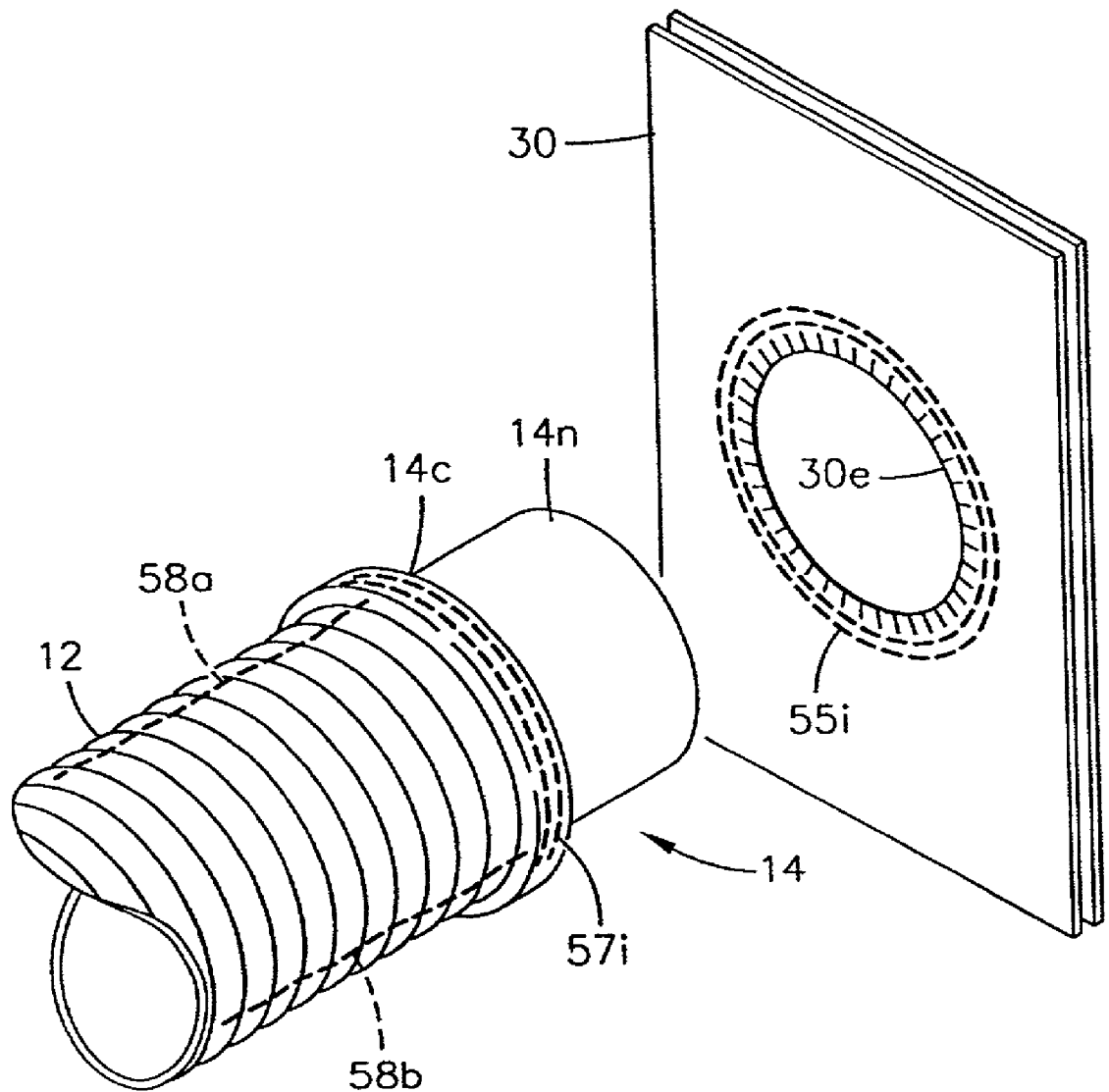
FIG. 7 illustrates another alternate embodiment of the presence sensor of FIGS. 3A and 3B.

Yet another implementation of the presence sensor is illustrated in FIG. 7 wherein the distal end 14 of the air hose 12 includes the nozzle 14n which transitions to a collar 14c within which a coil 57i is embedded. The coil 57i is connected to and driven by the conductors 58a and 58b. Disconnected from the hose card 30, the coil 57i exhibits an impedance having an electromagnetic characteristic (impedence, with an inductive component). A second coil 55i is embedded in the hose card 30e around the edge 30e. Now, when the distal end 14 of the air hose 12 is seated in the hose card so that the collar 14c is adjacent the edge 30e, the impedance driven by the conductors 58a and 58b has a value measurably different from that exhibited by the coil 57i when the distal end 14 is not seated in the hose card 30. Alternatively, the coils 57i and 55i could be replaced with insulated conductive elements that exhibit a measurable capacitance whose value changes when the distal end 14 and the inlet port 11 are connected and disconnected.

One way in which to measure a change in an electromagnetic characteristic at the junction between the distal end 14 and the inlet port 11 would be to drive the circuit 58a, 57i,58b with a signal of known frequency generated by the control unit 21. A change in the characteristic would be manifested by a change in frequency of the signal.

Another way in which to measure a change in an electromagnetic characteristic at the junction between the distal end 14 and the inlet port 11 would be to drive the circuit 58a, 57i,58b with a variable frequency signal that includes a known frequency generated by the control unit 21. A change in the characteristic would be manifested by a change in the impedance of the circuit at the known frequency of the signal.

Yet another implementation of the presence sensor is to imbed a small piece of magnetic material in the hose card. This material may be excited with a single pulse from circuit 58a, 57I, 58b. The activation of the magnetic material would then cause resonance in that material with a back scattering of a characteristic frequency. This frequency would then be sensed through the same activating circuit of 58a, 57I, 58b.

Figure 8A:
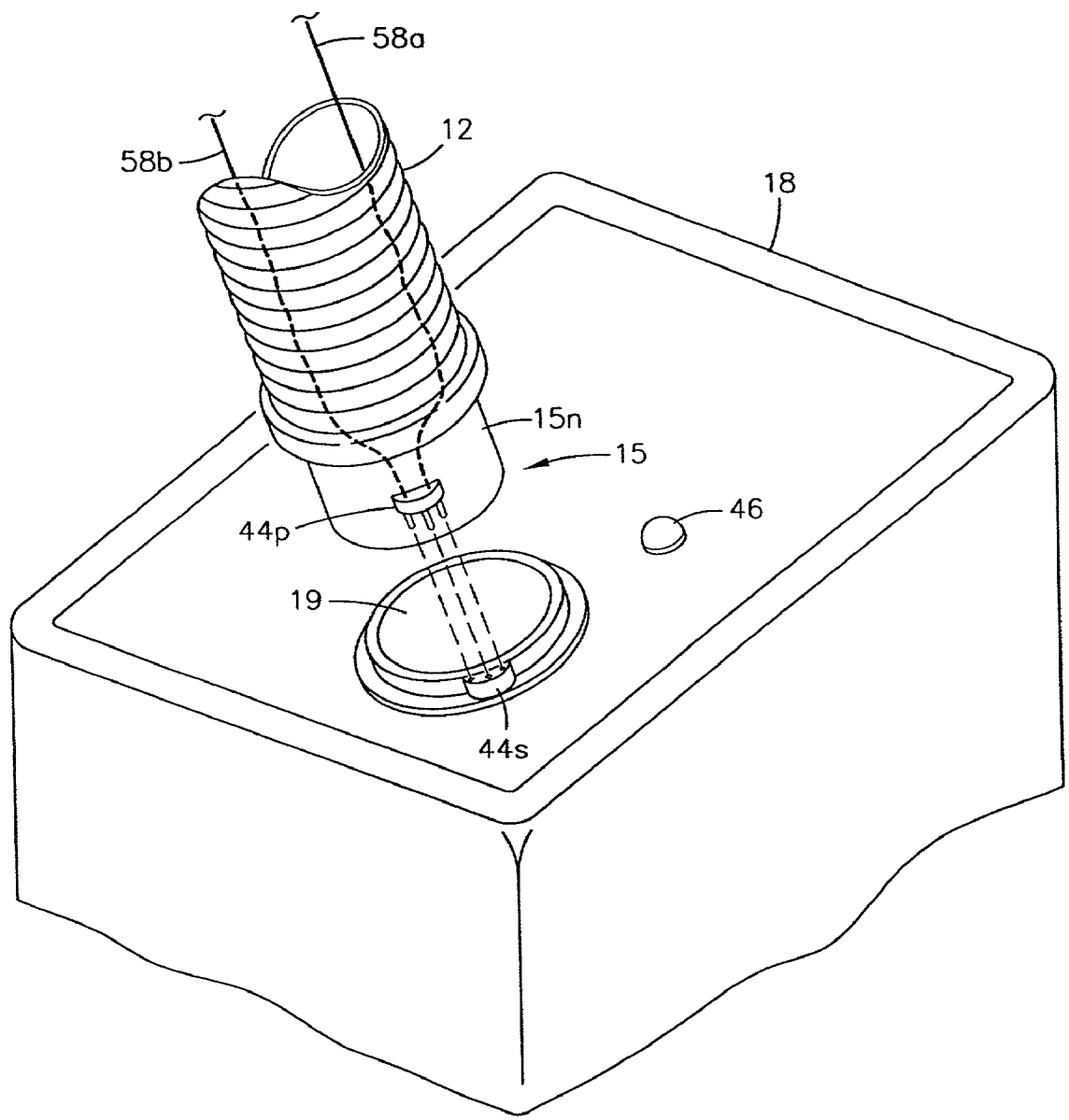
FIGS. 8A and 8B illustrate how the proximal end of the air hose may be coupled to a heater/blower unit.
Figure 8B:
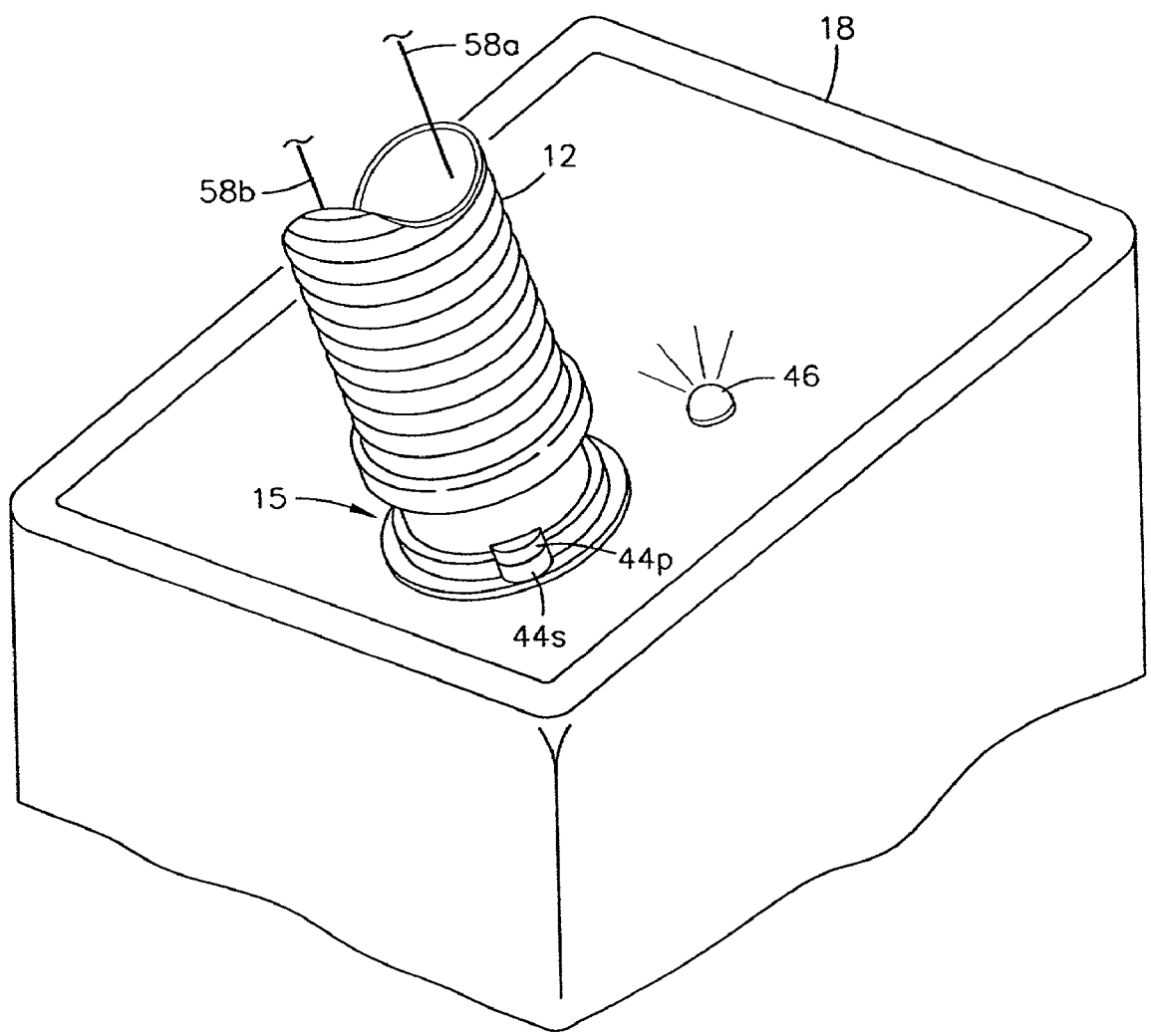

FIGS. 8A and 8B illustrate how a connection is made to the heater/blower unit 18 at the proximal end of 15 of the air hose 12, to provide continuity of a signal pathway to the control unit 21 (not shown). In this regard, a connector plug 44p is mounted on a proximal end nozzle 15n. The conductors 58a and 58b terminate on respective pins of the plug 44p. When the nozzle 15n is received in the port 19 of the unit 18, the pins of the plug 44p are received in respective receptacles of a connector socket 44s mounted on the unit 18, adjacent to the port 19, in alignment with the pins of the plug 14p. As shown in FIG. 8B, when the plug 44p and socket 44s are mated, the indicator 46 provides (in this example) a visual indication of joinder, mating, coupling, or connection between the distal end 14 of the air hose 12 and one of one or more inlet ports of an inflatable thermal device.

Figure 9:
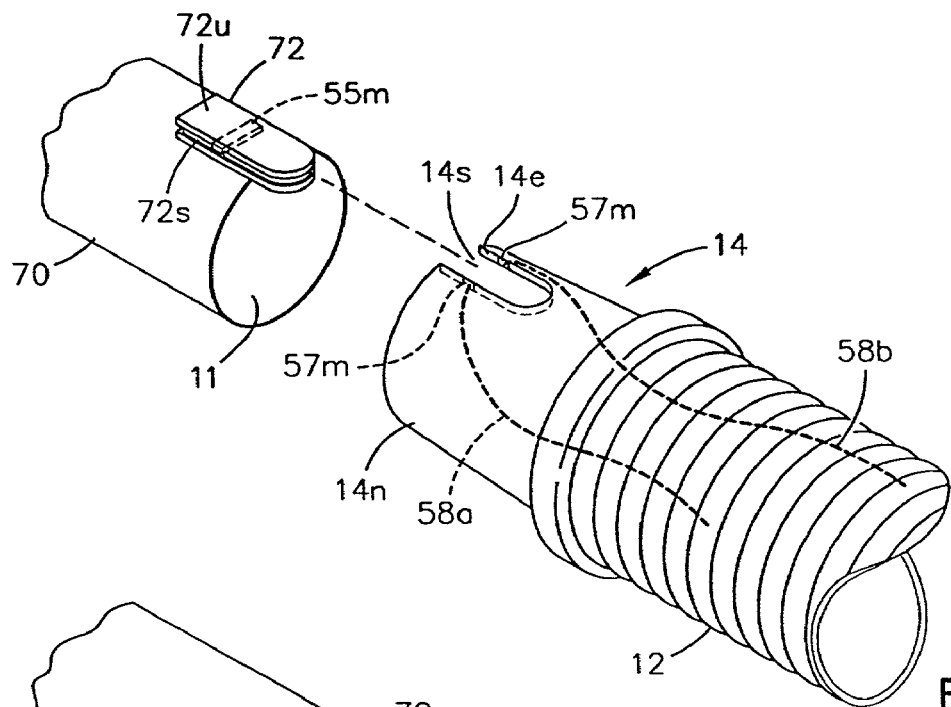
FIG. 9 shows a presence sensor in an inflatable thermal device in which an inlet port is provided as a sleeve.
Figure 10A:
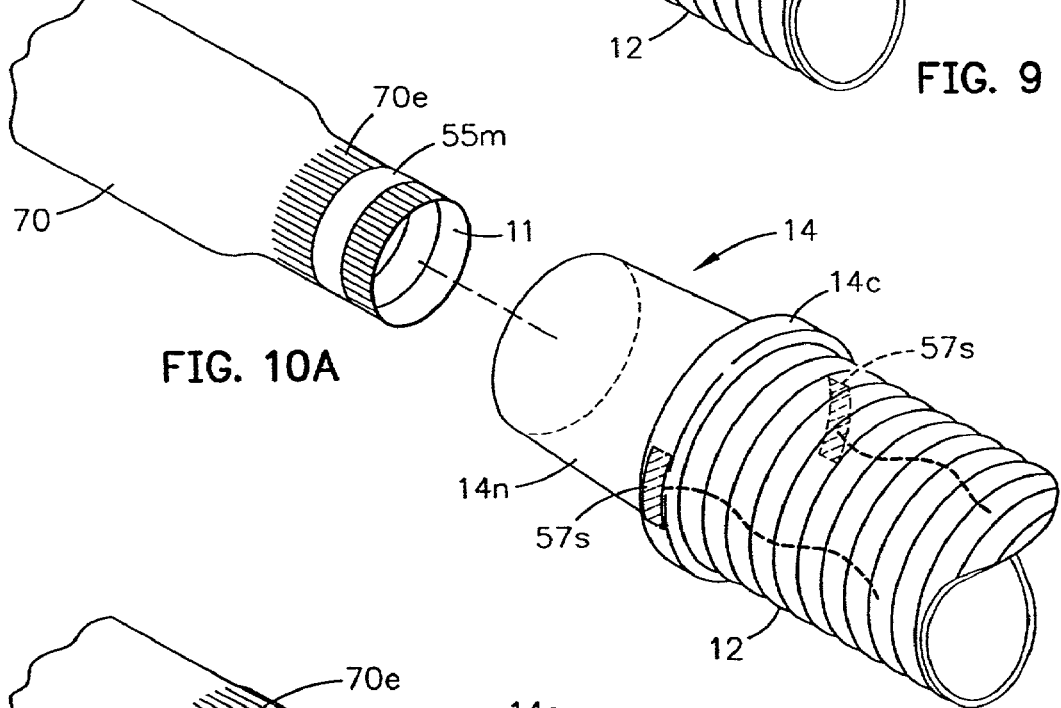
FIGS. 10A and 10B show an alternate embodiment of the presence detector of FIG. 9.
Figure 10B:
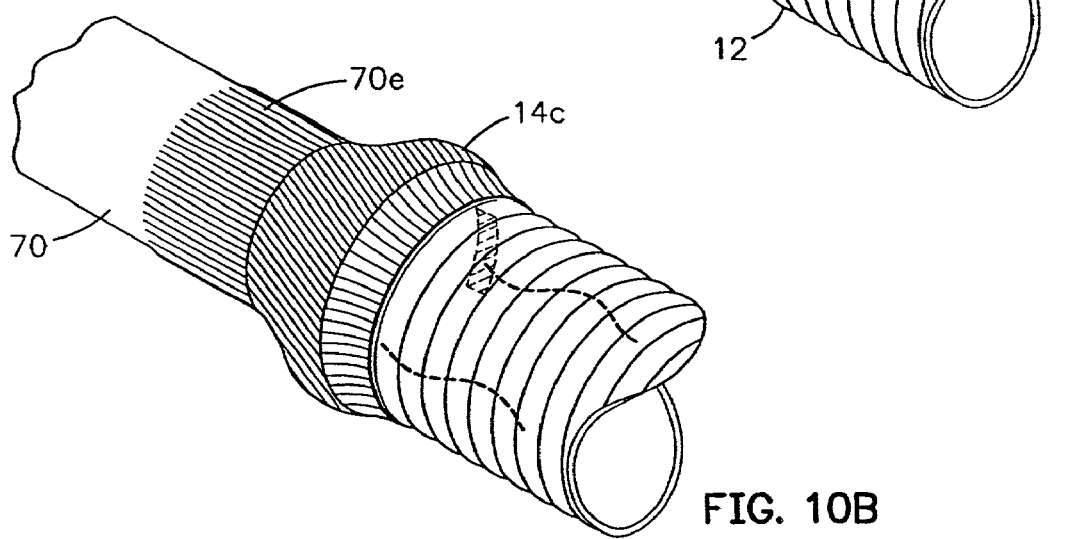

FIGS. 9, 10A and 10B illustrate inlet ports having sleeve-like constructions. Referring to FIG. 9, the distal end 14 of the air hose 12 has the nozzle 14n in which a slot 14s is cut. An edge 14e of the slot is exposed and elements of conductive material 57m are placed on the edge 14e, in opposition across the slot 14s. The inlet port 11 is embodied in a sleeve 70 of material that extends from and opens into an inflatable thermal device (not shown). An alignment and contact mechanism 72 is mounted on the inside of the sleeve 70 by appropriate means including, for example, gluing between the inside surface of the sleeve and the upper surface 72u of the alignment mechanism 72. The alignment mechanism 72 may be a molded plastic piece that generally has the shape of the slot 14s and includes a peripheral slot-like recess 72s that receives the edge 14e of the slot 14s. A strip of conductive material 55m is disposed in the alignment mechanism 72, protruding in the opposed places into the peripheral slot-like recess 72s. When the slot 14s is seated on the alignment mechanism 72, an electrical circuit is completed or closed between the conductive material elements 57m by way of the strip of conductive material 55m. In FIGS. 10A and 10B, the end of the sleeve 70 has an elastic material integrated into the material of the sleeve 70 to form an elastic portion 70e. On the inside surface of the elastic portion 70e a ring of conductive material 55m is attached. The distal end 14 of the air hose 12 has substantially the same construction as that illustrated in FIGS. 6A and 6B, with the exception that the circumferential groove 14g is omitted. To join, couple, the distal end 14 in the inlet port 11 via the sleeve 70, the elastic region 70e is expanded, and the distal end 14 is slid into the sleeve 70 until the collar 14c is in the portion of the elastic region 70e that is girded on its inside surface by the ring of conductive material 55m, which closes or otherwise completes an electrical pathway between the conductive elements 57s. The nozzle 14n is retained in the sleeve 70 by the grip of the elastic region 70e on the nozzle's outside surface.

FIGS. 11A through 11C illustrate the inflatable thermal device where the inlet port 100 includes a hose card 102. It should be understood that the inlet port 100 and hose card 102 are typically a component of an inflatable thermal device which is not shown as an effort to simplify the drawings. The hose card 102 is used to provide the first circuit element electrical connection and to provide mechanical stability to the air hose/inlet port interface. As shown in FIGS. 6A, 6B, 7, 10A, and 10B, the first circuit element 104 is annular, surrounding the inlet port 100. This permits the first, or distal end 106 of air hose 108 to freely rotate in the inlet port 100 without a loss of electrical continuity. The first hose end also includes the second circuit element, two electrical contacts 110a and 110b are shown, but in some aspects the second circuit element is a single electrical contact. The second circuit element 110a/110b cooperates with the first circuit element to enable a signal representing a connection between the first end 106 of the air hose 108 and the inlet port 100. As mentioned above, the connection is made independent of the rotational alignment of the air hose in the inlet port. The rotational alignment is represented by reference designator 112. In a simple aspect, the first 104 and second 110a/110b circuit elements are electrical contacts, the joining of which completes an electrical circuit, signifying that the air hose 108 is properly mated in the inlet port 100. As is explained in more detail below, that connection of first 104 and second 110a/110b circuit elements can be used to conduct signals with information content which permit a more complex determination of the condition of the air hose 108 in the inlet port 100.

In one aspect, as shown, the first circuit is made up of a plurality of members, such as member 114, which have a saw-tooth shape ending in a peak pointing toward the center of the inlet port 100. Typically, the hose card is made of cardboard, or some similarly pliable material so that as the air hose first end 106 is inserted in the inlet port 100, the members 114 are deformed. Due to the tooth shape of the members 114, which increases in thickness in moving towards the base of the tooth, the members gradually stiffen as the first hose end 106 is inserted.

FIG. 11B illustrates the hose card 102 of FIG. 11A with a mated hose 108. It is well known for the diameter of a hose to gradually increase in travel from the end for the purpose of making a snug connection with a mating port. One advantage of such a connection is the elimination of intermittent connection events which would be a nuisance for operators. Another advantage is in ensuring a reliable electrical connection, or a consistent value of resistance generated between deforming members 114 and second circuit elements 110a and 110b.

FIG. 11C is a cross-sectional view of the air hose 108 of FIG. 11B illustrating a modification to better receive the deformable members 114. An annular groove 116 is formed in the first hose end around the outside diameter. The second circuit element 110a is seated the groove 116. As the air hose 108 is inserted into the inlet port 110, the members 114 are bent. The mechanical, and therefore electrical, connection between the first circuit element 104 and the second circuit element 110a is captured by the action of the stiffened members 114, as well as by the bent shape of the members 114.

To complete the electrical connection required for the first 104 and second 110a/110b circuit elements to cooperate, the first circuit element deformable members 114 have a surface coated with a conductive ink. The ink can include conductive elements such as copper, silver, and carbon, but is not limited to the use of just the named connective elements. One conductive ink found to be effective is manufactured by Acheson, under the part number of SS 24600. The conductive ink can be formulated to have a known resistance, permitting the controller to differentiate between different types of thermal devices. For example, it may be desirable to have the controller operate the blower under a first set of temperature and airflow parameters when a first kind of inflatable thermal device, having a first resistance measurement, is connected to the air hose. The control circuit is able to measure and recognize different resistance values, correlate these resistance measurements to corresponding inflatable thermal devices, and modify the temperature and airflow parameters in response to the measured resistance, so that a variety of inflatable thermal device can be operated at predetermined parameters from a single blower unit.

Figure 12A:
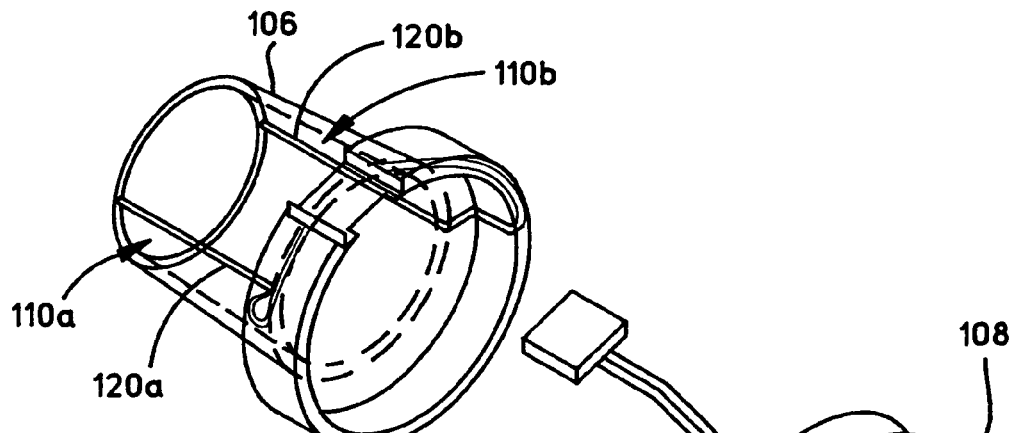
FIGS. 12A through 12C illustrate an alternate aspect of the air hose of FIG. 11A or the air hose of FIGS. 6A, 6B, 7, 10A, and 10B.
Figure 12B:
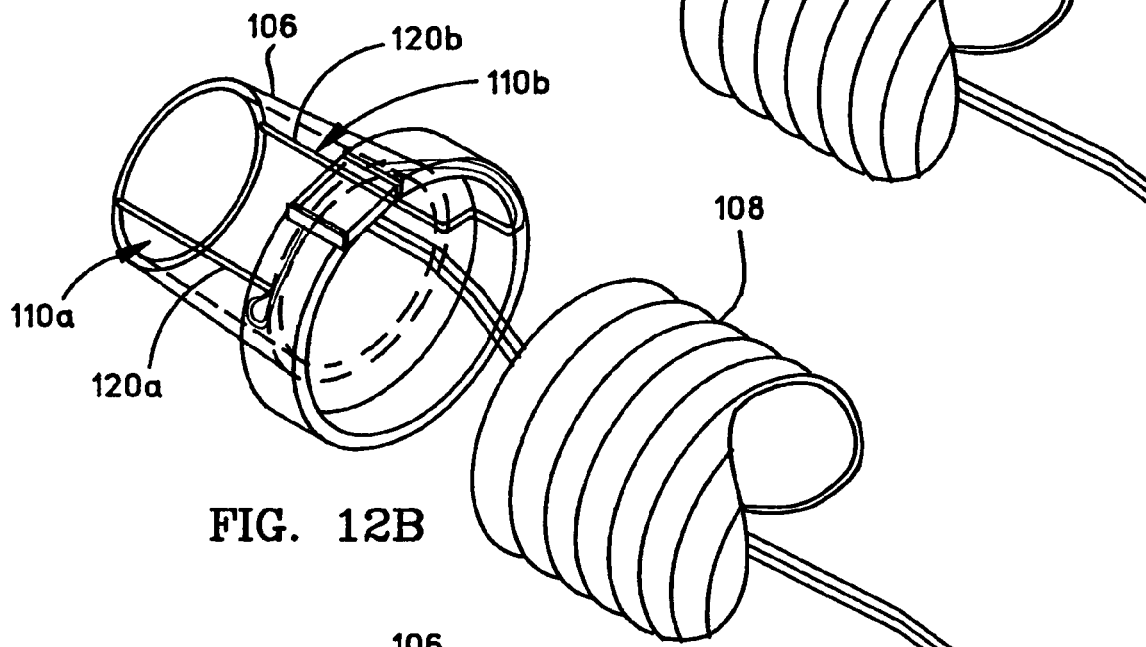
Figure 12C:
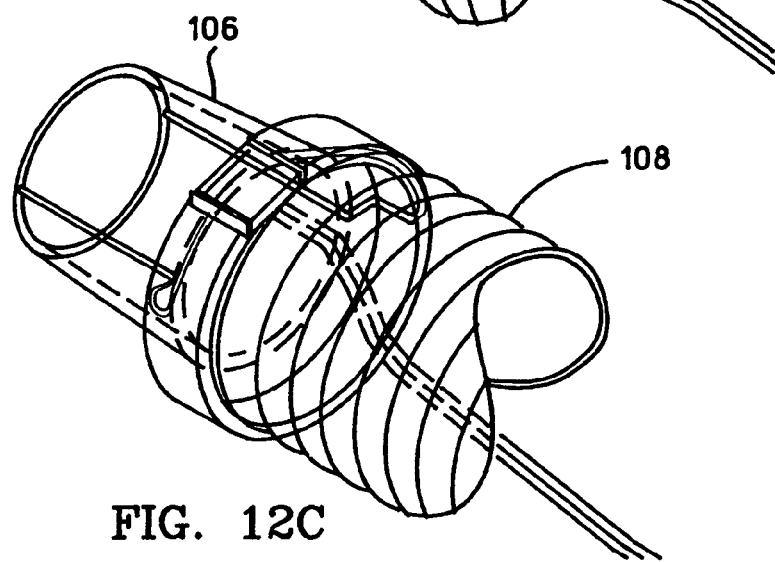

FIGS. 12A through 12C illustrate an alternate aspect of the air hose 108 of FIG. 11A or the air hose 12 of FIGS. 6A, 6B, 7, 10A, and 10B. That is, the second circuit element to be described can be used with a variety of first circuit element designs, including the hose card first circuit element. The air hose first end 106 is manufactured from a partially resistive material, such as a conductive polymer, in which electrical conductivity can be varied by loading the material with conductants such as carbon. These materials have a surface conductivity in-between standard plastics and metal. Conductive polymers are lighter than metal, and less subject to denting. The PermaStat® family of products manufactured by the RTP company is an example of such a material. The second circuit element is formed from a highly conductive element, such as metallic wire which is embedded in the polymer material. Two conductive elements 120a and 120b are shown. Electrical current can pass from the polymer nozzle surface to the embedded wires 120a/120b, with the electrical resistance being at a minimum at the surface area immediately overlying the wires. That is, the second circuit element includes the conductive elements 120a/120b and the polymer surface overlying the elements. Further, the first circuit element 104 and second circuit element 110a/110b cooperate to enable a signal between the first circuit element (however defined) and the polymer hose surface immediately overlying the highly conductive element 120a/120b. In other aspects, the polymer surface overlying the conductive elements 120a/120b is formed in a separate fabrication process from the deposition of the conductive elements and/or the formation of supporting layer of nozzle material that need not be the highly resistive polymer.

Regardless of whether the first circuit element is a simple electrical contact, a contact as described in the explanation of FIGS. 6A, 6B, 7, 10A, and 10B, or the hose card design described in the explanation of FIGS. 11A–11C, the impedance, resistivity, or conductance across the element can be measured and defined as a first impedance. Likewise, regardless of whether the second circuit element is as described in FIGS. 6A, 6B, 7, 10A, 10B, 11A–C, or 12A–C, the impedance can be measured and defined as the second impedance. Then, the cooperation of the first 104 and second 110a/110b circuit elements provides an impedance which represents a connection between the first end of the hose and the inlet port. That is, the combination of impedances represents a condition where the air hose 108 is properly connected to the inlet port 100. Too small an impedance could represent an improper connection or a short. Too large an impedance typically represents a disconnection in the cable connecting the sensor to the controller circuitry, such as the air hose 108 being improperly mated to inlet port 100. In some aspects, the first impedance may be significantly larger than the second impedance, so that in measuring the series line impedance of a properly mated air hose 108, the contribution of the second impedance to the measurement is of no consequence. In other aspects, the second impedance is significantly larger than the first impedance.

The impedance across the conductive ink first circuit element 104 of hose card 102 (FIGS. 11A–11C) is modified by the amount of conductant material in the ink, the conductive path, the ink thickness, or the stiffness of the members 114 when seated against air hose first end 106. Likewise, the conductivity of second circuit element 110a/110b of FIGS. 12A–12C is modified by how far the conductive elements 120*a*/120*b* are buried in the polymer and the specific conductivity of the polymer material.

In other aspects (not shown), the air hose has a shape to encourage a particular alignment. That is, the air hose must be rotated to specific position to insert the air hose into the inlet port. In these circumstances the first circuit element no longer need be annular in shape. Further, since the position of the second circuit element contacts are predetermined, the first circuit element can be shaped to bridge the gap between the second circuit element contacts.

Figure 13B:
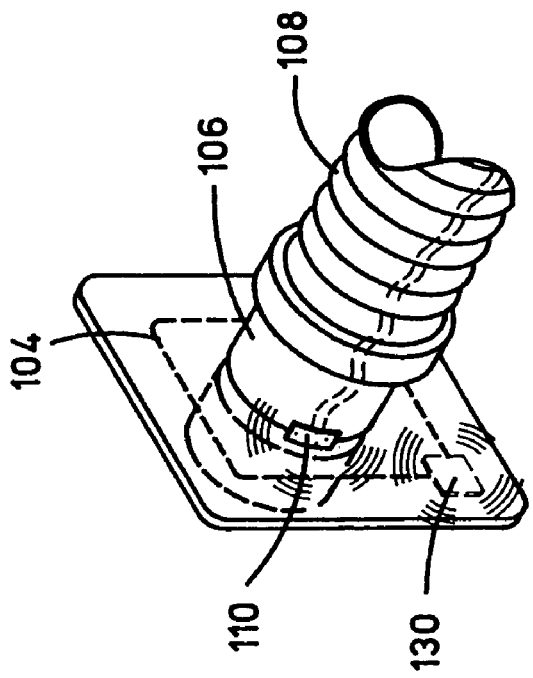
FIGS. 13A and 13B illustrate a convective warming system using an electronic identification tag.
Figure 13A:
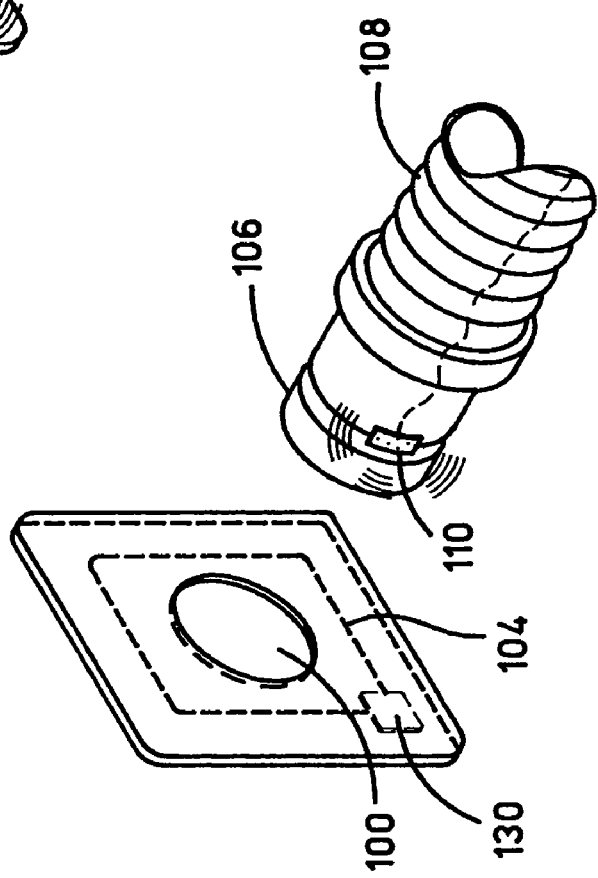

FIGS. 13A and 13B illustrate an convective warming system using an electronic identification tag 130. The electronic tag 130 provides information. In its simplest form, the tag 130 provides a single bit of information that is used to communicate that an electrical connection has been made. This aspect is similar in concept to the impedance measurement method described above in the explanation of FIGS. 12A–12C. In other aspects the electronic tag 130 provides more information, which in turn, permits a wider range of responses.

Communication with the electronic identification tag 130 can be made through a direct-wired-connection, through a modulated magnetically radiated signal, and a modulated electrically radiated signal. When a direct electrical connection is to be made, any of the above-described methods to interface the first 104 and second 110 circuit elements can be used. However, when radiated signals are to be used, the first 104 and second 110 circuit elements must be radiating elements, or antennas, as shown. Interrogation and identification signals are coupled between radiating elements 104 and 110. When radiated signals are used the electronic identification tags are often called radio frequency identifiers (RF IDs). The higher frequency electric fields can generally be propagated a further distance than the magnetic fields, given the same amount of transmit energy. It may be desirable to limit interrogations from the second circuit element 110, so that the air hose does not communicate with neighboring inflatable thermal devices outfitted with RF IDs.

The first circuit element 104 at an inlet port of the inflatable device is connected to the electronic identification tag 130 to identify the inflatable device. The second circuit element 110 near the first end 106 of an air hose 108 is receivable in the inlet port 100. The second circuit element 110 cooperates with the first circuit element 104 to enable an identification signal. As mentioned above, the identification signal may just represent a connection between the air hose first end 106 and the inlet port 100. In these circumstances the electronic identification tag provides a 1-bit identification message.

Alternately, the identification can contain more information bits. At present, electronic identification tags which provide a 64-bit identification code are common, but are not limited to any particular message length. Among other things, the multiple-bit message can provide information which describes the inflatable thermal device model number, the inflatable thermal device serial number, the preferred air flow rate, the preferred air temperature, and patient identification. The air flow, temperature, and other parameters can be regulated in response to knowing this information. For example, the preferred air flow characteristics may differ for different inflatable thermal device models. Alternately, the tag 130 can be loaded to provide the patients identity, the number of times the blanket has been connected to the warming unit, and the amount of time the blanket has been in use. The air flow controlling mechanism can regulate air flow in response to local database of patient characteristics, or the air flow can be established in communication between the air flow controller and a central system. In other aspects, the electronic tag is worn by the patient. In some aspects the electronic tag supplies updated patient vital statistics which are downloaded through the air flow controller to a local file, or communicated to the central system.

The electronic tag must be powered to transmit a signal. The power can be maintained at the inflatable thermal device. That is, the first circuit element 104 includes a power supply (not shown) directly connected to the electronic identification tag 130. Alternately, the second circuit is directly connected to the power source. Through coupling between radiating elements 104 and 110, the second circuit element 110 cooperates with the first circuit element 104 to power the electronic identification tag 130.

FIGS. 14A, 14B, 15A–15C, 16A, and 16B illustrate some examples of mechanical solutions to the problem of controlling air flow to an inflatable thermal device according to the invention. These solutions rely on the act of coupling the air hose into the inlet port to open a valve and permit the flow of air. Likewise, the decoupling of the air hose from the inlet port causes the valve to close, preventing burn accidents or improper operation of the equipment. These solution do not rely upon the engagement of electrical contacts, the relaying of electrical signals, or electronic identification for the system to convectively control the temperature of an inflatable thermal device.

Figure 14A:
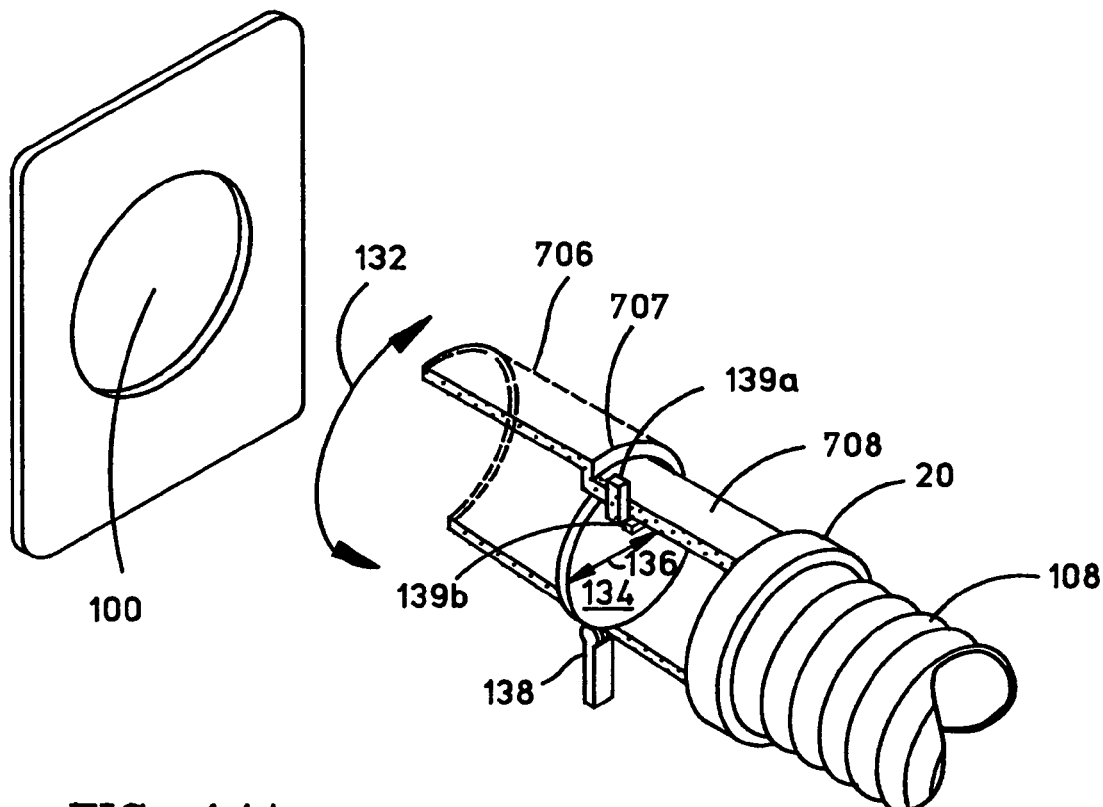
FIGS. 14A, 14B, 15A–15C, 16A, and 16B illustrate alternate embodiments of mechanical solutions to the problem of controlling air flow to an inflatable thermal device according to the invention.
Figure 14B:
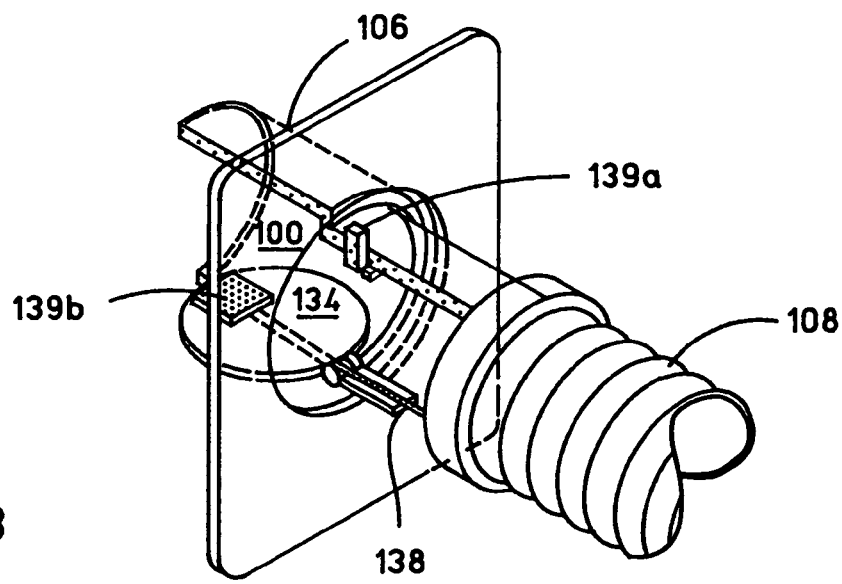

FIG. 14A depicts an inflatable device inlet port 100. The first end 106 of the mating air hose 108 includes a valve 130. As seen in FIG. 14B, as first end 106 of air hose 108 is received in the inlet port 100, the valve 130 cooperating with the inlet port to enable airflow between the hose first end 106 and the inlet port 100. Also, while FIG. 14B depicts the valve flap 136 opening toward the inlet port 100 upon activation, it is also possible to design a valve system in which the flap 136 opens towards the hose 108 upon activation. It should also be noted that the valve is engaged independent of the rotational alignment 132 of the air hose 108 in the inlet port 100. That is, there is no single, or keyed position in which the valve operates.

The valve 130 includes two primary components, a flap 134 which has a diameter 136 substantially the same as the inner diameter of the air hose first end 106, or at least the air hose diameter that interfaces with the flap. It should be noted that the flap 134 need not perfectly seal the air hose 108 to be effective. The flap 134 blocks the flow of air, or substantially blocks the flow of air, when the air hose 108 is not received in the inlet port 100. The other main component of the valve 130 is the actuating mechanism, of which three examples are shown.

As depicted in FIGS. 14A and 14B, in one aspect of the invention the valve 130 includes a hinge lever 138 which is rigidly attached to the flap. At the intersection of the hinge lever 138 and flap 134 is an axle or pin (not shown) about which the flap 134 and hinge level 138 pivot. The hinge lever 138 cooperates with the inlet port 100, moving from a position perpendicular to the air hose 108, to a position against the air hose 108, to permit the hose first end 106 to fit inside the inlet port 100. The engagement of the hinge lever 138 prevents the flap 134 from blocking the flow of air when the air hose first end 106 is received in the inlet port 100. Not specifically shown is the mechanism which returns the flap 134 to the blocking position (FIG. 14A) when the air hose 108 is not engaged in the inlet port 100. The return-mechanism can be a spring or some such torsioning member (not shown) which is put under load by the action of the flap being forced into the open position (FIG. 14B). Additionally, in some orientations, the valve flap can be returned to its seated position by the frictional force of the airflow within the air hose 108. Once the valve flap 136 is seated, it will be held in place by the static pressure developed by the blower.

In some aspects of the invention a pair of magnets 139a and 139b are used to keep the flap 134 in the blocking position when the air hose 108 is not received in the inlet port 100. The air hose 108 includes the first magnet 139a, and the valve flap 134 includes the second magnet 139b. The first magnet 139a cooperates with the second magnet 139b so that the flap 134 blocks the flow of air when the air hose 108 is not received in the inlet port 100. Although not specifically shown, magnets can also be used with the flap 134 of the actuator mechanisms shown in FIG. 15A, described below. In another aspect of the invention, not shown, the flap 134 is opened in the direction of the air hose 108 instead of the inlet port 100, so that the flow of air through hose 108 acts to close the flap 134 when it is not engaged.

Figure 15A:
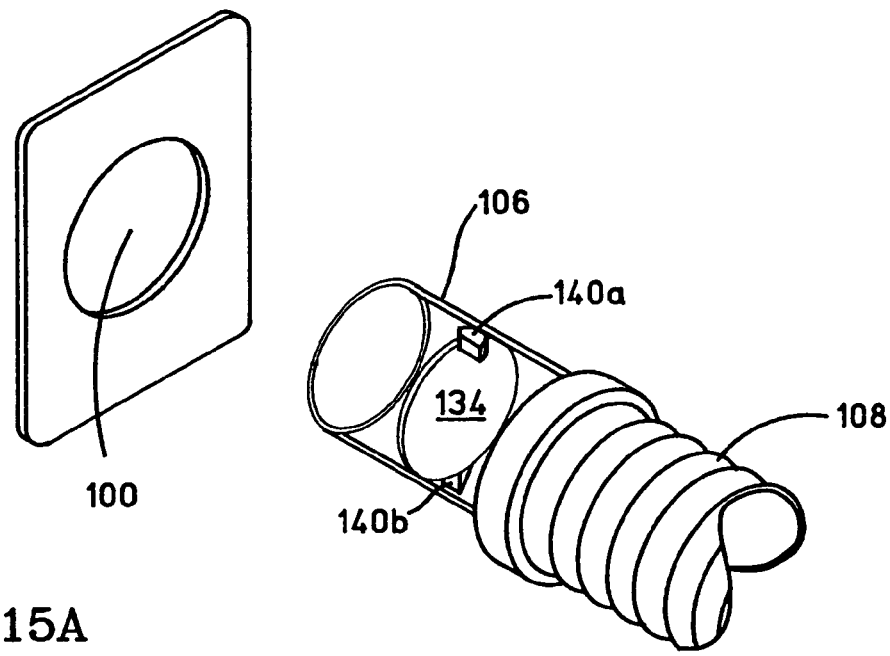
Figure 15B:
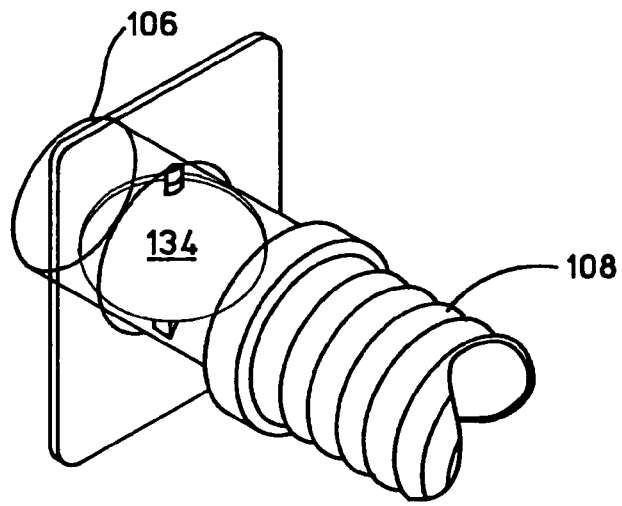
Figure 15C:
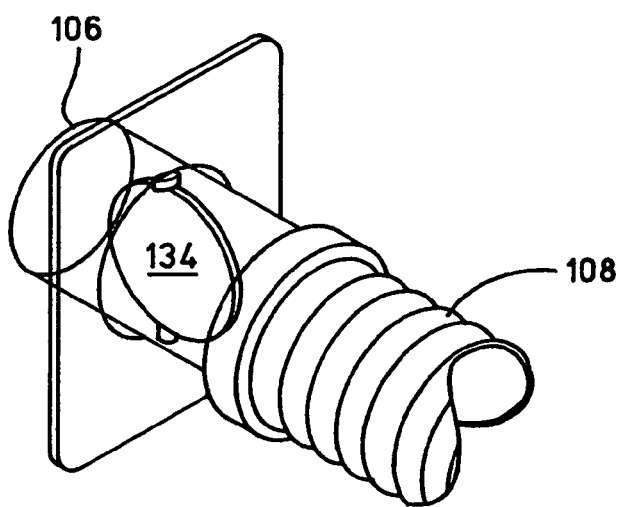

FIGS. 15A through 15C depict the valve flap 134 of FIG. 14A, with a cam actuation mechanism. As shown in FIG. 15A, the flap 134 includes a pair of cams 140a and 140b rigidly attached to the flap 134, 180 degrees apart. Alternately, the cam can be attached to an axle running through the diameter of the flap 134, with the axle being rigidly attached to the flap, so that the face of the flap and the cam facets remain in a fixed relationship. The cam includes rounded surfaces which permit the cams 140a/140b, and attached flap 134, to rotate as the cam engages the surface surrounding the inlet port 100. The rotation of the cams 140a/140b is shown if FIG. 15B. As shown in FIG. 15C, the flat facet surfaces of the cams 140a/140b permit those surfaces to fixedly seat against the inlet port as the air hose 108 is engaged. With the cams 140a/140b seated, the flap 134 is locked in an open position to permit the flow of air. Not shown is the return mechanism which forces the flap 134 into the blocking position (FIG. 15A). As above, the return mechanism can be a spring, or the like that is put under load as the flap is forced into the open (non-blocking) position.

Figure 16A:
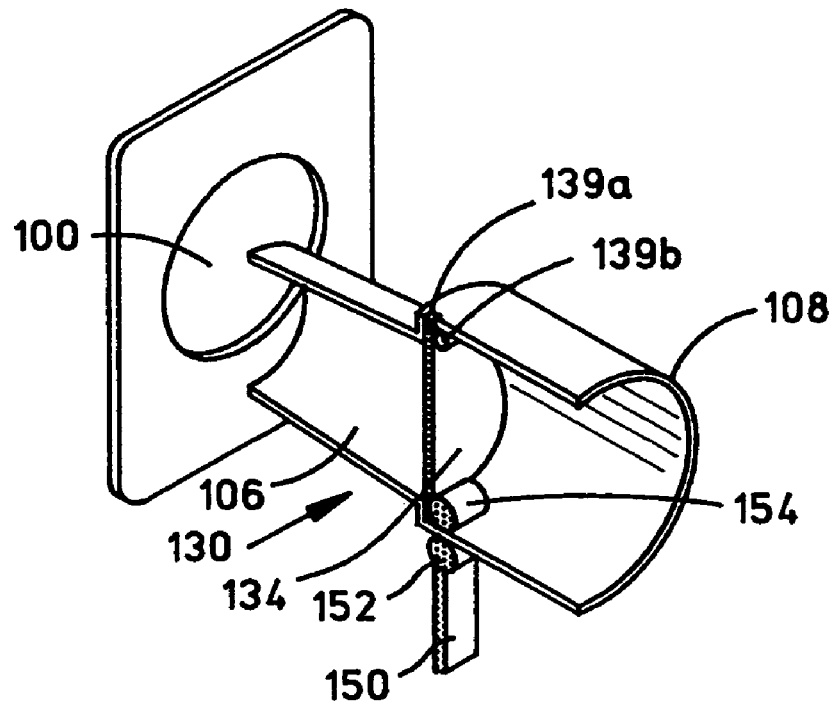
Figure 16B:
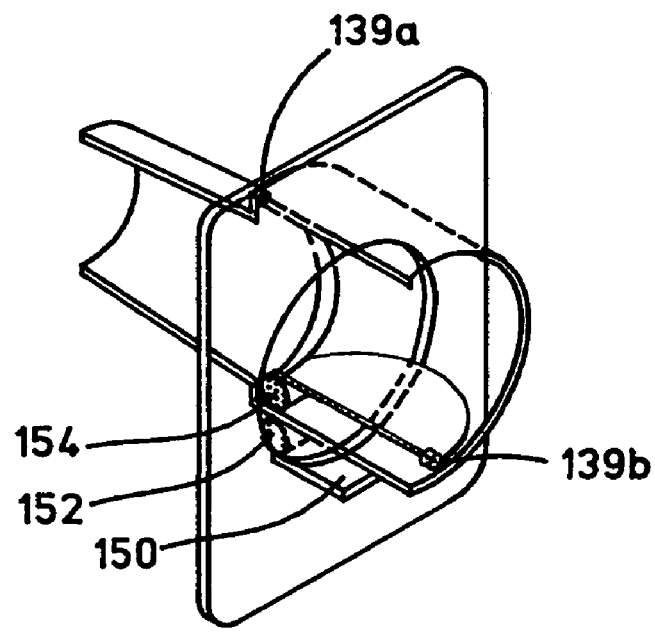

FIGS. 16A and 16B depict the gear rack valve actuator mechanism. The mechanism includes a lever 150 which engages the inlet port to open the flap 134. Lever 150 is connected to a first gear 152, the teeth of which are intermeshed with the teeth of a second gear 154. In turn, the second gear 154 is attached to flap 134. As the lever is engaged, it is forced into the body of the hose 108. The action of the lever 150 and the gears 152/154 open the flap 134 so that air can pass through the hose 108 into inlet port 100. In some aspects of the invention a pair of magnets 139a/139b are used to keep the flap 134 in the blocking position when the air hose 108 is not received in the inlet port 100. In other aspects, the opening of the flap 134 into the direction of the airflow acts to force the flap 134 into a blocking position when level 150 is not engaged in inlet port 100.

Figure 17:
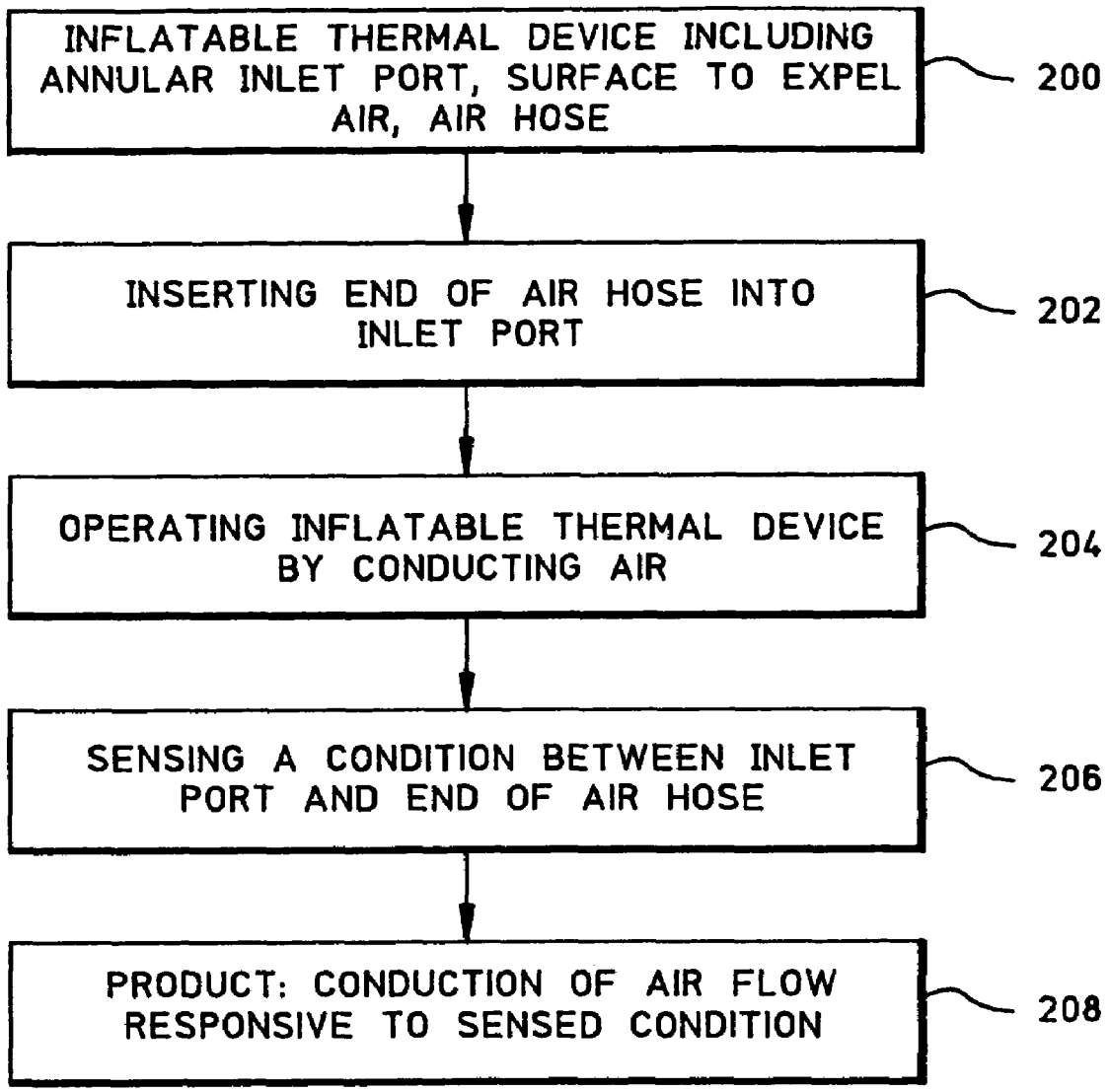
FIG. 17 is a flowchart illustrating a method for controlling air flow in a system including an inflatable thermal device, corresponding to FIGS. 14A–14B, 15A–15C, and 16A–16B.
Figure 18:
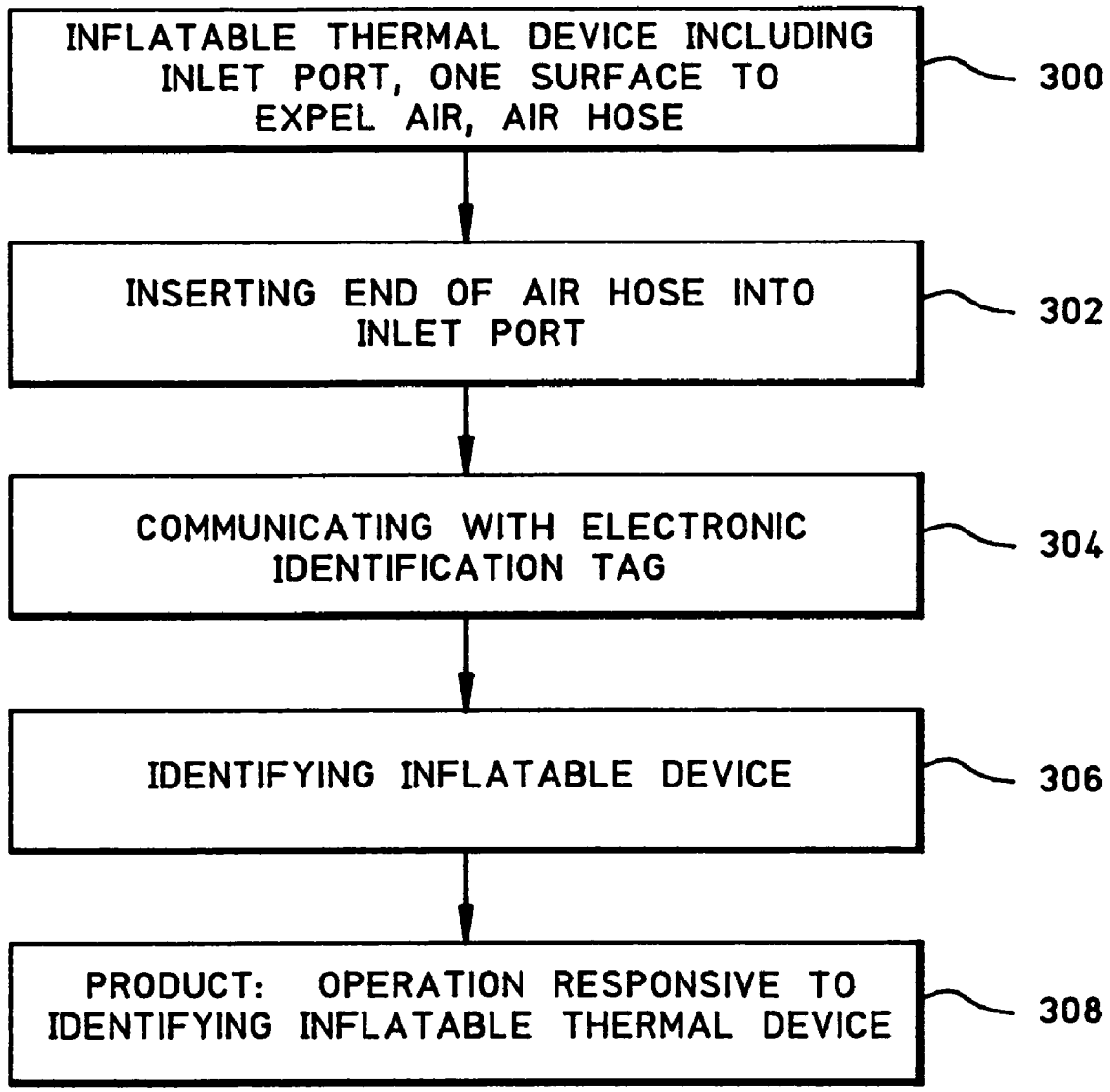
Figure 19:
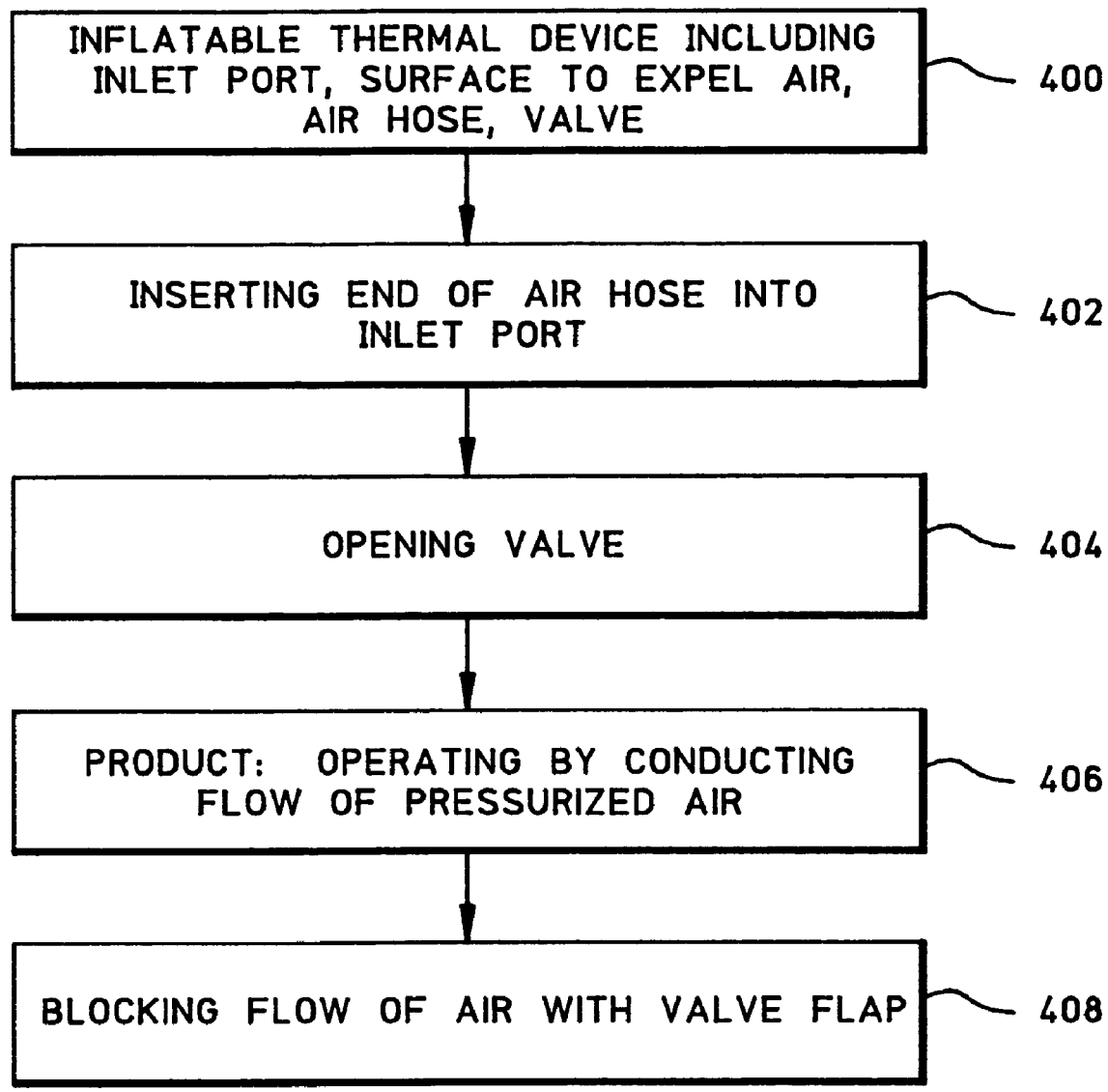

FIG. 17 is a flowchart illustrating a method for controlling air flow in a system including an inflatable thermal device, corresponding to FIGS. 14A–14B, 15A–15C, and 16A–16B. Step 400 includes the inflatable thermal device having at least one inlet port, at least one surface adapted to expel air, and an air hose having two ends and a valve to prevent the delivery of a flow of pressurized air to the inflatable thermal device. Step 402 inserts an end of the air hose into the inlet port of the inflatable thermal device. Step 404, in response to inserting the air hose into the inlet port, opens the valve. The opening of the valve in Step 404 includes the valve cooperating with the inlet port. Step 406 is a product where the inflatable thermal device is operated by conducting a flow of pressurized air through the air hose.

Step 400 includes a valve having a flap with a diameter that is substantially the same as the air hose first end diameter. The method further comprises Step 408. Step 408 blocks the flow of air with the valve flap when the air hose is not received in the inlet port.

In some aspects of the invention Step 400 includes a valve with a hinge lever. Then, the opening of the valve in Step 404 includes the hinge lever cooperating with the inlet port to prevent the flap from blocking the flow of air when the air hose is received in the inlet port.

In some aspects of the invention Step 400 includes a valve with seating cams. Then, the opening of the valve in Step 404 includes the seating cams cooperating with the inlet port acting to prevent the flap from blocking the flow of air when the air hose is received in the inlet port.

In other aspects, Step 400 includes an air hose with a first magnet and a valve flap includes a second magnet. Then, the blocking of the air flow in Step 408 includes the first magnet cooperating with the second magnet, positioning the flap to prevent the flow of air when the air hose is not received in the inlet port.

In some aspects of the invention Step 402 includes making an electrical connection when the air hose end is inserted into the inlet port. As described in detail above, the electrical connection can be an on/off determination, an impedance measurement, or inflatable thermal device identification. Then, Step 406 includes operating the inflatable device by delivering the pressurized air in accordance with parameters that are responsive to the electrical connection made. For example, the inflatable device could be supplied with no air, or less heat, if an electrical connection is not made, regardless of whether the flap is open. Otherwise, the parameters of the airflow such as rate and temperature can be varied in responsive to an impedance measurement, or digital identification of the inflatable thermal device.

Clearly, other embodiments and modifications of the present invention will occur readily to those of ordinary skill in the art in view of these teachings. For example, inflatable thermal devices may have more than one inlet port. Also, a heater/blower unit with more than one air hose may fall within the scope of this invention. Further, the invention may be applied to convective systems having the elements of FIG. 1 that cool persons, animals, or things. Therefore, this invention is to be limited only by the following claims, which include all such embodiments and modifications.

We claim:

1. A combination for controlling airflow between an air hose and an inflatable thermal blanket, comprising:
    an end of the air hose having a diameter;
    at least one inlet port in the inflatable thermal blanket for being coupled with the end of the air hose;
    at least one planar hose card attached to the inflatable thermal blanket, the planar hose card including an aperture aligned with an inlet port for receiving and supporting the end of the air hose when the end is coupled with the inlet port;
    a valve with a flap having a diameter substantially the same as the end diameter and disposed in the air hose near the end for opening to enable airflow out of the end when the end is coupled with the aperture and the inlet port; and
    means near the end for opening the flap in response to the aperture and the inlet port coupling with the end;

the means including a moveable hinge lever connected to the flap which moves from a first position away from the end to a second position against the end in response to the end being coupled with the aperture and the inlet port;

the flap being prevented from blocking the flow of air when the hinge lever is in the second position.

2. The combination of claim 1, further including a first magnet in the air hose, and a second magnet on the flap, wherein the first magnet cooperates with the second magnet to enable the flap to block the flow of air when the end is not coupled with the aperture and the inlet port.

3. A combination for controlling airflow between an air hose and an inflatable thermal blanket, comprising:

an end of the air hose having a diameter;

at least one inlet port in the inflatable thermal blanket for being coupled with the end of the air hose;

at least one planar hose card attached to the inflatable thermal blanket, the planar hose card including an aperture aligned with an inlet port for receiving and supporting the end of the air hose when the end is coupled with the inlet port;

a valve with a flap having a diameter substantially the same as the end diameter disposed in the air hose near the end for opening to enable airflow out of the end when the end is coupled with the aperture in the hose card and the inlet port; and means near the end for opening the flap in response to the inlet port coupling with the aperture and the end;

the means including a first magnet in the air hose, and a second magnet on the flap, wherein the first magnet cooperates with the second magnet to enable the flap to block the flow of air when the end is not coupled with the aperture and the inlet port.

4. A method for controlling air flow in a system including an inflatable thermal blanket, an air hose having two ends, at least one inlet port in the inflatable thermal device for receiving one end of the air hose, at least one planar hose card attached to the inflatable thermal blanket, the planar hose card including an aperture aligned with an inlet port for receiving and supporting the end of the air hose when the end is coupled with the inlet port, a flap in the air hose near the one end, and a hinge lever in the air hose near the one end, the hinge lever attached to the flap, the method comprising:

inserting the one end through the aperture in the planar hose card;

coupling the one end with the inlet port;

moving the hinge lever against the air hose in response to coupling;

moving the flap in response to movement of the hinge lever in order to permit an airflow out of the one end;

the hinge lever cooperating with the inlet port to prevent the flap from blocking airflow;

operating the inflatable thermal device in response to the airflow;

decoupling the one end from the aperture and the inlet port; and, in response to decoupling, moving the hinge lever away from the air hose;

the flap being moved to block airflow through the one end in response to the hinge lever moving away from the air hose.

5. The method of claim 4, in which the system also has a first magnet in the air hose and a second magnet on the flap, the method further including the first magnet cooperating with the second magnet to enable the flap to block the flow of air when the end is decoupled from the aperture and the inlet port.

6. A method for controlling air flow in a system including an inflatable thermal blanket, an air hose having two ends, at least one inlet port in the inflatable thermal device for receiving one end of the air hose, at least one planar hose card attached to the inflatable thermal blanket, the planar hose card including an aperture aligned with an inlet port for receiving and supporting the end of the air hose when the end is coupled with the inlet port, the air hose including a flap near the one end, a first magnet in the air hose and a second magnet on the flap, the method comprising:

coupling the one end with the aperture in the planar hose card and the inlet port;

moving the flap in response to coupling in order to permit an airflow out of the one end;

operating the inflatable thermal device in response to the airflow;

decoupling the one end from the inlet port and the aperture; and, in response to decoupling, moving the flap to block airflow through the one end;

the first magnet cooperating with the second magnet to retain the flap in a position in the one end at which the flap blocks airflow through the one end.

* * * * *

UNITED STATES PATENT AND TRADEMARK OFFICE
CERTIFICATE OF CORRECTION

| | |
|---|---|
| PATENT NO. | : 7,220,273 B2 |
| APPLICATION NO. | : 10/024387 |
| DATED | : May 22, 2007 |
| INVENTOR(S) | : Van Duren et al. |

It is certified that error appears in the above-identified patent and that said Letters Patent is hereby corrected as shown below:

Item (56) References Cited

Page 2, left column, under the heading U.S. PATENT DOCUMENTS:

Immediately preceding "5,716,721 A * 2/1998 Moysan et al. .... 428/627", please add:

--5,716,271 A * 2/1998 Paidosh ............ 454/359--

Signed and Sealed this

Twentieth Day of May, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,220,273 B2 | Page 1 of 2 |
| APPLICATION NO. | : 10/024387 | |
| DATED | : May 22, 2007 | |
| INVENTOR(S) | : Van Duren et al. | |

It is certified that error appears in the above-identified patent and that said Letters Patent is hereby corrected as shown below:

Title Page, Item [73]
Delete the additional "," inserted after "Inc.,".

Column 1, line 25
After the word "or" delete the word "hypothermia" and replace it with "hyperthermia".

Column 1, lines 33-35
Starting with the word "Particular" and ending with the word "use", italicize this title.

Column 3, line 53
Delete the word "and".

Column 3, line 55
After the number "9" delete "." and replace it with ";".

Column 3, line 57
After the word "card" delete "." and replace it with ";".

Column 3, line 60
After the number "10B" delete "." and replace it with ";".

Column 3, line 62
After the word "tag" delete "." and replace it with ";".

Column 3, line 66
After the word "invention" delete "." and replace it with "; and".

Column 6, line 22
Delete the number "111" and replace it with "11".

Signed and Sealed this
Third Day of July, 2012

David J. Kappos
*Director of the United States Patent and Trademark Office*

CERTIFICATE OF CORRECTION (continued)
U.S. Pat. No. 7,220,273 B2

<u>Column 7, line 58</u>
Delete the word "Aair" and replace it with "air".

After the word "sensor" delete the "≅".

<u>Column 9, line 13</u>
Delete the number "500" and replace it with "50o".

<u>Column 13, line 11</u>
Delete the word "an" and replace it with "a".

<u>Column 15, line 31</u>
Delete the word "if" and replace it with "as".

Claim 4, column 17, line 37, delete "thermal device" and replace it with "thermal blanket".

Claim 4, column 18, line 8, delete "thermal device" and replace it with "thermal blanket".

Claim 6, column 18, line 25, delete "thermal device" and replace it with "thermal blanket".

Claim 6, column 18, line 37, delete "thermal device" and replace it with "thermal blanket".